United States Patent
Buckman et al.

(10) Patent No.: US 7,017,195 B2
(45) Date of Patent: Mar. 28, 2006

(54) AIR BAG INFLATION DEVICE

(76) Inventors: Robert F. Buckman, 125 Chew La., Radnor, PA (US) 19087-5207; Jay A. Lenker, 408 Panorama Dr., Laguna Beach, CA (US) 92651; Donald J. Kolehmainen, 6 Crested Butte Cir., Laguna Niguel, CA (US) 92677

( * ) Notice: Subject to any disclaimer, the term of this patent is extended or adjusted under 35 U.S.C. 154(b) by 0 days.

(21) Appl. No.: 10/741,639

(22) Filed: Dec. 18, 2003

(65) Prior Publication Data

US 2004/0183283 A1    Sep. 23, 2004

Related U.S. Application Data

(60) Provisional application No. 60/434,732, filed on Dec. 18, 2002.

(51) Int. Cl.
*A61G 9/00* (2006.01)
(52) U.S. Cl. .................. 2/455; 2/465; 2/468; 2/DIG. 3; 280/730.1
(58) Field of Classification Search .............. 2/DIG. 3, 2/463, 465, 467, 468, 92, 102, 462, 455, 2/456, 413, DIG. 10, 22; 280/728.1, 730.1; 340/573.1
See application file for complete search history.

(56) References Cited

U.S. PATENT DOCUMENTS

| 4,977,623 | A |   | 12/1990 | DeMarco ........................ 2/69 |
| 5,497,511 | A | * | 3/1996 | Zade ............................... 2/22 |
| 5,500,952 | A | * | 3/1996 | Keyes ............................ 2/465 |
| 5,539,935 | A | * | 7/1996 | Rush, III ....................... 2/422 |
| 5,593,111 | A | * | 1/1997 | Jackson et al. ......... 244/110 D |
| 5,937,443 | A | * | 8/1999 | Kageyama et al. .............. 2/69 |
| 6,032,299 | A |   | 3/2000 | Welsh ........................... 2/456 |
| 6,160,478 | A | * | 12/2000 | Jacobsen et al. ....... 340/539.12 |
| 6,166,639 | A | * | 12/2000 | Pierce et al. ............. 340/573.1 |
| 6,201,476 | B1 | * | 3/2001 | Depeursinge et al. .... 340/573.1 |
| 6,208,251 | B1 | * | 3/2001 | Cadet et al. ............. 340/573.1 |

(Continued)

FOREIGN PATENT DOCUMENTS

DE     4003683 A1 *   8/1991

(Continued)

*Primary Examiner*—Rodney M. Lindsey
(74) *Attorney, Agent, or Firm*—K. David Crockett, Esq.; Niky Economy Syrengelas, Esq.; Crockett & Crockett

(57) ABSTRACT

This invention relates to active protective garments which are inconspicuously worn by an individual and which activate upon certain conditions being met. Activation causes inflation of regions of the active protective garment to provide padding and impact cushioning for the wearer.

The invention is an active protective garment such as pair of shorts or pants, a jacket, a vest, underwear, and the like. The garments comprise multiple layers of material that constrain pockets or regions that are inflatable by a source of compressed gas or foam. The garments also comprise sensors to detect ballistic parameters such as acceleration, distance, relative acceleration, and rotation. The sensor information is used to determine whether activation is required. Detection and activation are accomplished in a very short time period in order to offer maximal protection for the individual wearing the garment. The system comprises a computer or logic controller that monitors the sensor data in real time and coordinates the information from all sensors. The system calculates velocity, distance, and rotational velocity. A rule-based system is used to detect a complex fall in progress and discriminate said fall in progress from the events of every day life. The pockets or inflatable regions of the garment protect the individual against falls and other impacts that may cause bone fracture or organ damage.

13 Claims, 10 Drawing Sheets

U.S. PATENT DOCUMENTS

| | | | |
|---|---|---|---|
| 6,270,386 B1 * | 8/2001 | Visocekas | 441/80 |
| 6,386,576 B1 * | 5/2002 | Kamen et al. | 280/728.1 |
| 6,418,564 B1 * | 7/2002 | Sheridan | 2/425 |
| 6,570,503 B1 * | 5/2003 | Ulert et al. | 340/573.1 |
| 6,611,783 B1 * | 8/2003 | Kelly et al. | 702/150 |
| 6,722,692 B1 * | 4/2004 | Fukaya et al. | 280/730.1 |
| 6,783,153 B1 * | 8/2004 | Mattes | 280/735 |
| 6,828,697 B1 * | 12/2004 | Mattes | 307/116 |
| 2001/0049840 A1 * | 12/2001 | Atanasio | 2/456 |
| 2002/0078484 A1 * | 6/2002 | Ulert et al. | 2/22 |
| 2003/0197608 A1 * | 10/2003 | Rudhard et al. | 340/539.18 |
| 2003/0214408 A1 * | 11/2003 | Grajales et al. | 340/573.1 |
| 2004/0003455 A1 * | 1/2004 | Davidson | 2/455 |
| 2004/0111790 A1 * | 6/2004 | Dainese | 2/456 |

FOREIGN PATENT DOCUMENTS

| | | |
|---|---|---|
| DE | 19744808 | 4/1999 |
| DE | 19838022 C1 * | 5/2000 |
| GB | 2312369 A * | 10/1997 |
| JP | 200051379 | 2/2000 |
| WO | WO 9101658 A1 * | 2/1991 |
| WO | WO 00051453 A1 * | 9/2000 |

* cited by examiner

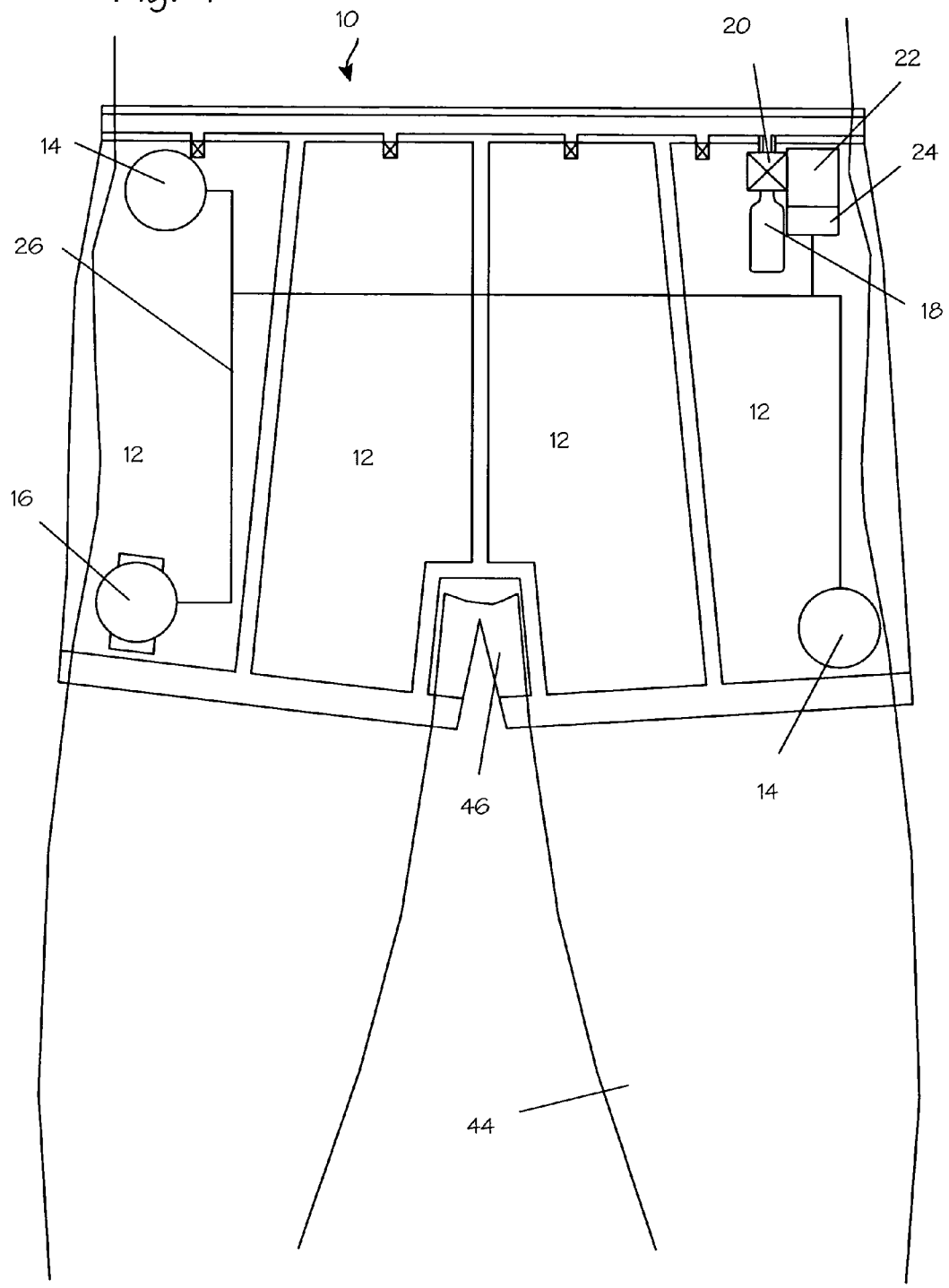

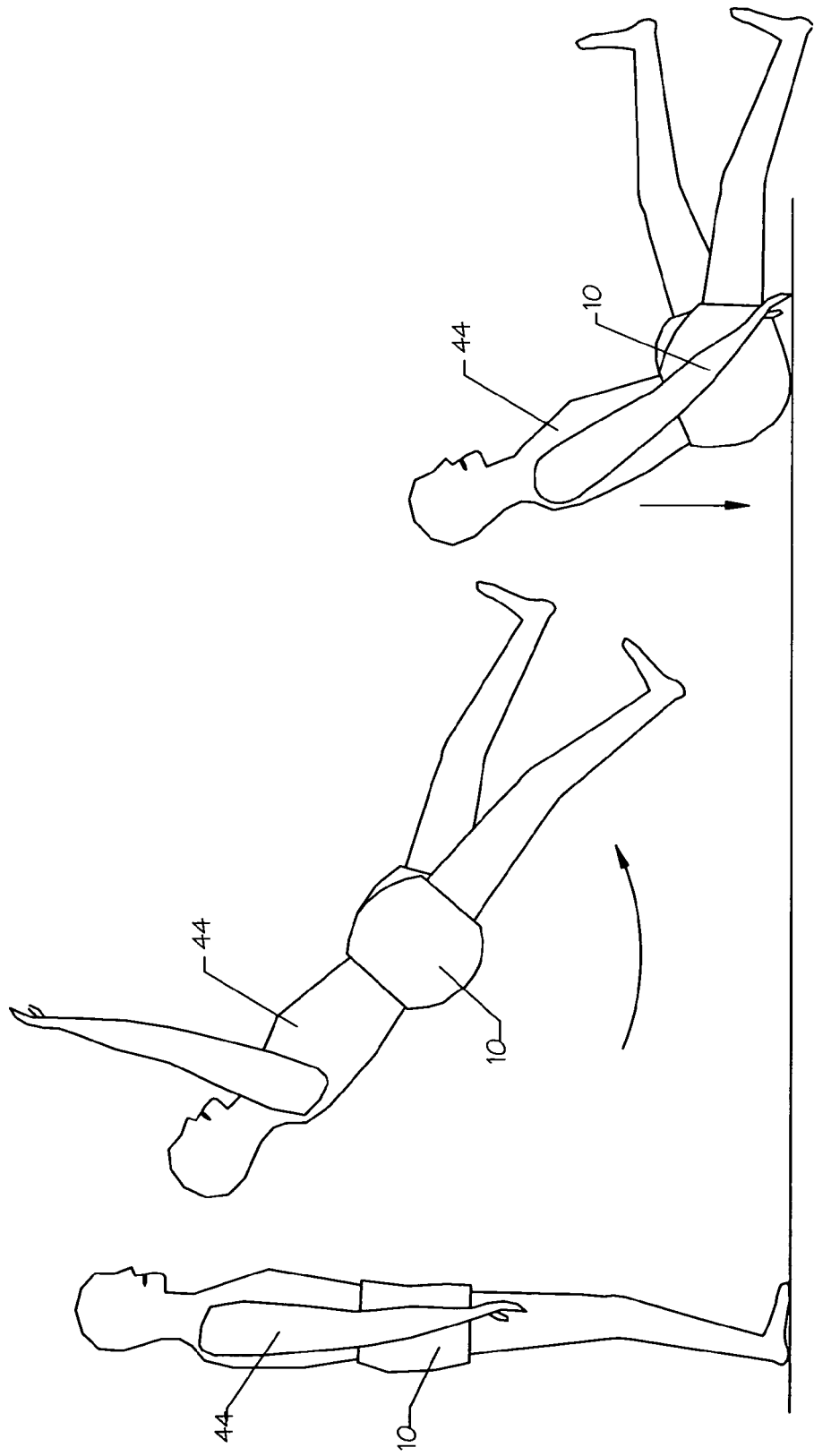

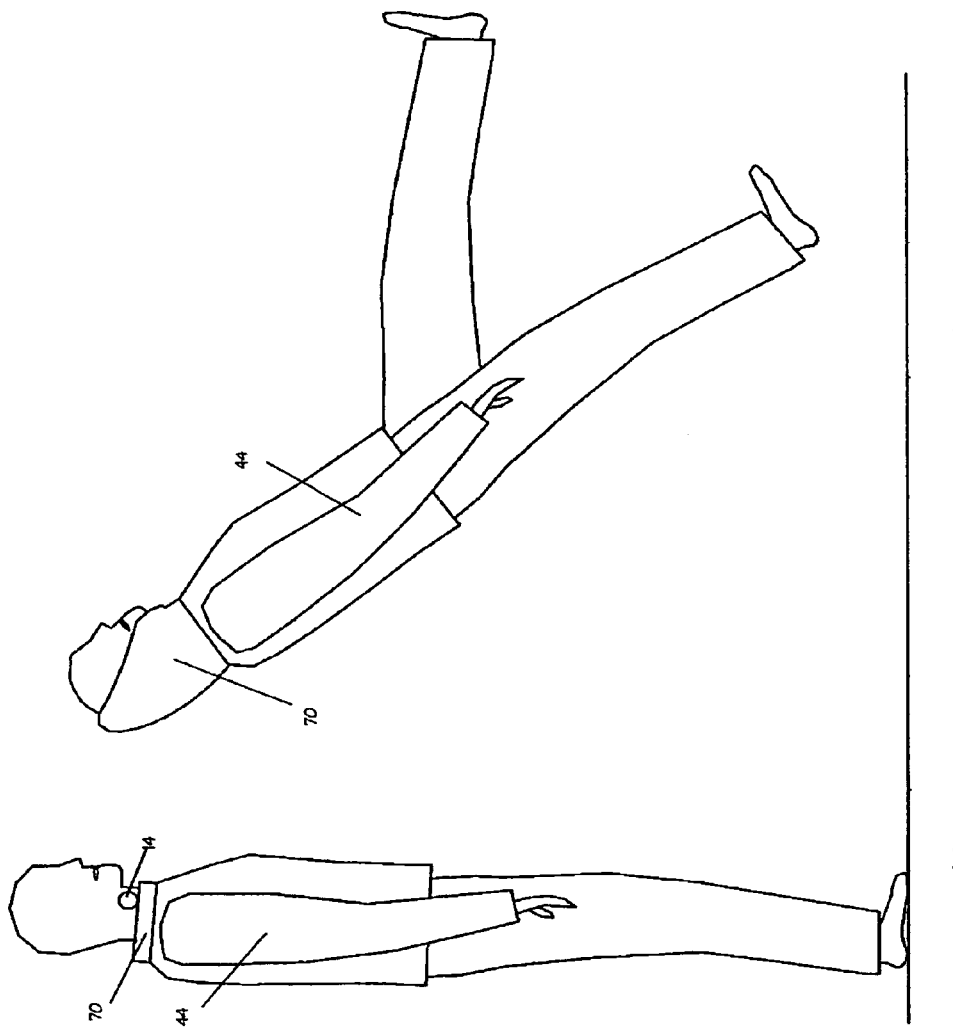

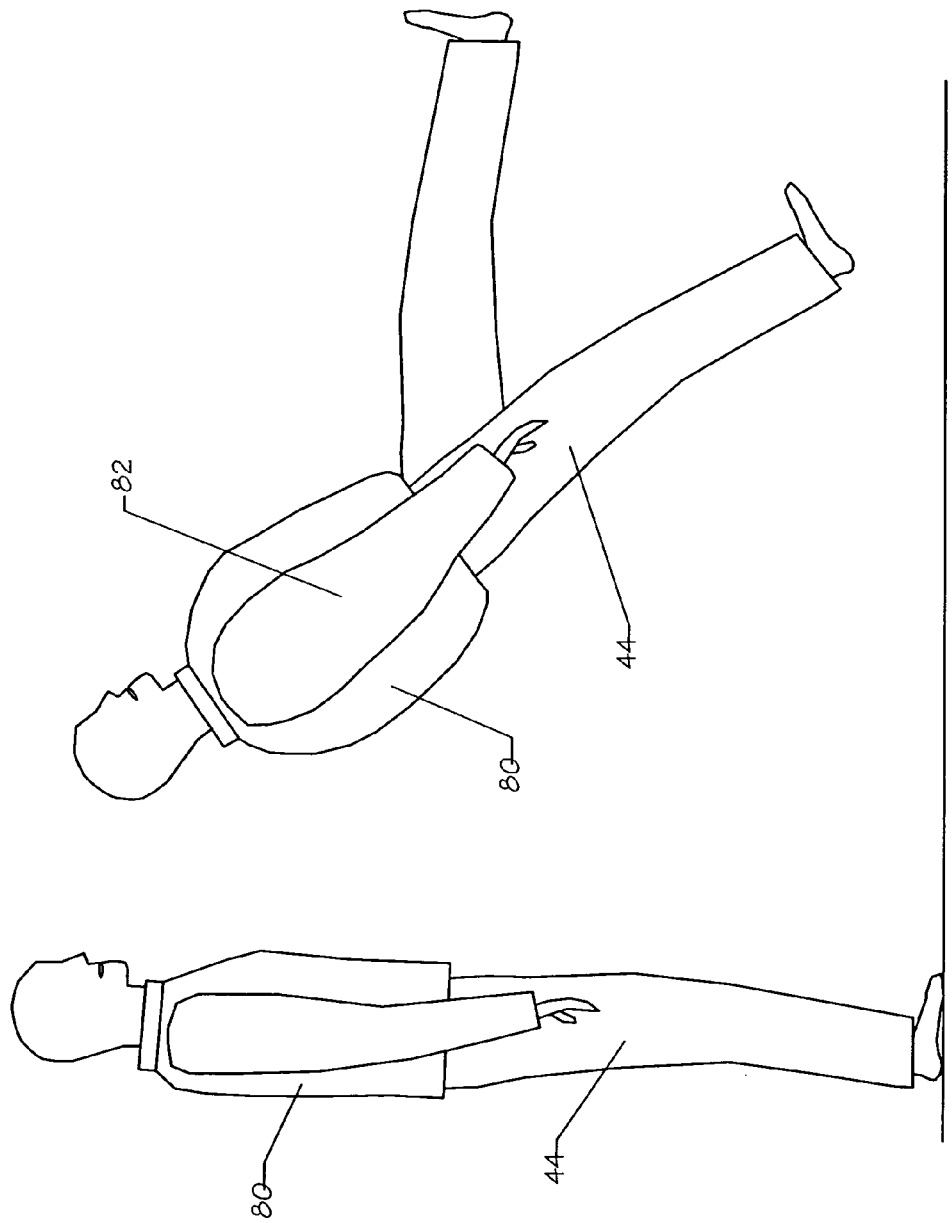

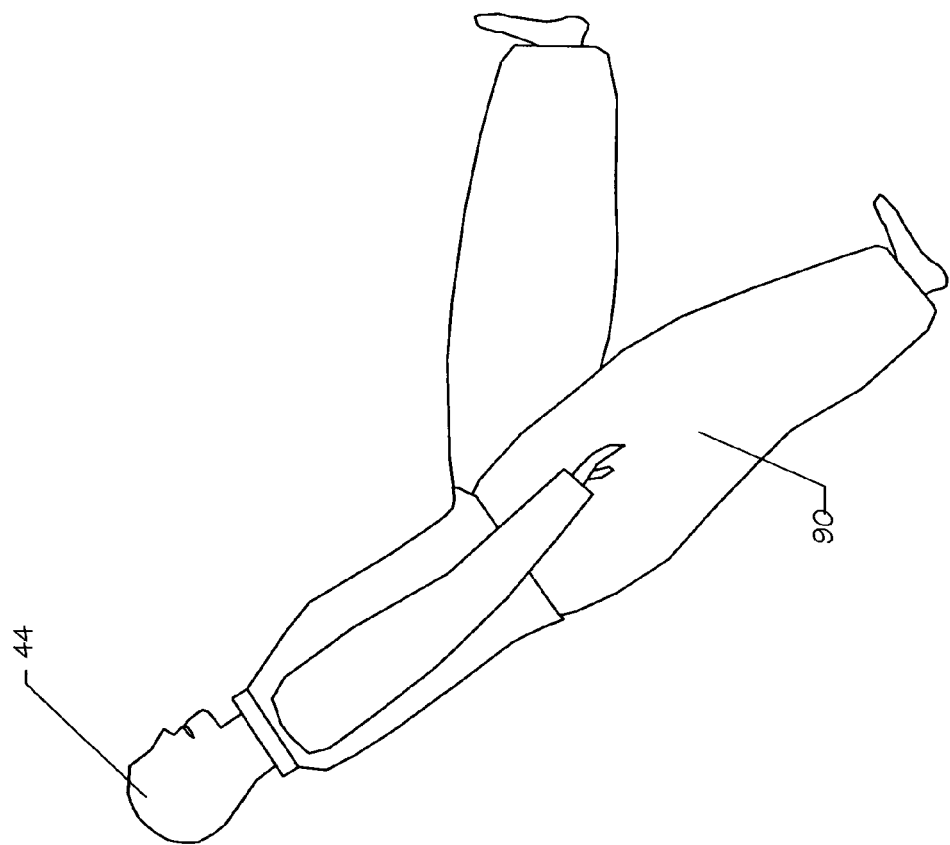
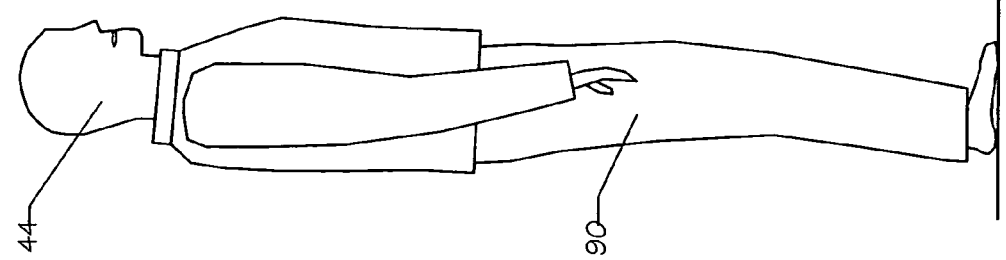

AIR BAG INFLATION DEVICE

This application claims priority benefit under 35 USC § 119(e) from U.S. Provisional Application No. 60/434,732 filed Dec. 18, 2002.

FIELD OF THE INVENTIONS

The inventions described below relate to devices and methods for protecting the body from injuries that result from impacts and falls, especially in elderly persons via the use of an air bag inflation device.

BACKGROUND OF THE INVENTIONS

Two of the common effects of aging are the onset of osteoporosis or other degenerative bone disease and the impairment of balance so that falls are frequent and often the cause of serious injuries in the elderly. In particular, fracture of the hip and pelvis are extremely common in older people. Such fractures can occur when a stationary or walking person falls when standing or sitting, if a person falls out of bed, or if a person falls down steps. Additionally, serious impacts may occur if a person is involved in a vehicular accident where velocities are considerably higher.

Persons who experience a hip or pelvic fracture often require hip-nailing or replacement surgery. While such repairs are often quite satisfactory, they are expensive and cause a significant financial drain on the health care system. In addition, patients who experience a hip fracture often experience compromised physiological function as a result of the fracture. In some cases, a patient may die as a result of the hip fracture and its sequelae. Among survivors, a fracture to the hip may also start a downward spiral in health that ultimately may lead to loss of independence and necessitating admission to a nursing home. Although fracture of the hip or pelvis is an injury characteristic and common to falling, many other injuries, especially of the brain, cervical spine, arms, and ribs are also common. Falls are, thus, a major cause of mortality and morbidity.

A person who falls once is often more likely to experience follow-on falls and, potentially, fractures. Such people are clearly at risk and could be identified as being at risk. People can also experience fractures when falling from trees, when skiing, rock-climbing, boating, riding bicycles, or pursuing many day-to-day activities.

In addition, people break more than hips when they fall. Fracture of bones in the neck, the spine, the skull, the arms, and the legs are not uncommon. Ligamentous and muscular injuries can also occur as a result of an impact as can internal organ damage. Even brain damage can result from impacts to the skull.

There are no satisfactory devices available today to protect persons from falls or other impacts in such a way that bone fracture may be prevented during every day activities. While people might wear body armor, helmets and the like, such armor and helmets would be too heavy, bulky, unattractive, and cumbersome for people to be willing to wear on a regular basis.

New devices, systems, and methods are needed to recognize when an individual is falling in order to protect them from the fall or other impacts that might lead to bone fracture and other serious injuries. Such devices are particularly important in the elderly where bone structure and balance may be compromised.

SUMMARY

This invention relates to active devices, fall-sensors and personal airbags used in garments and clothing designed to protect an individual from an impact injury, especially those due to accidental falls.

The invention is an active protective system or active protection garment (APG) that includes detection, activation, and protection mechanisms. The protection mechanism is automatically deployed via an air bag inflator when sensors detect the accelerations, directions or rotations associated with the early phases of an accidental fall. The active protection system comprises a garment that is worn by a person or animal requiring protection. The garment may be, depending on the part of the body to be protected, a vest, coat, hat, helmet, pants, shorts, underpants, shirt, undershirt; jumpsuit, shoes, socks, scarf, or other clothing. The system or garment may further comprise elements added to conventional articles of clothing. The garment, or added elements, comprises structures, analogous to an airbag, that are capable of inflating or expanding to provide protection to the wearer. The garment, or added elements, further includes sensors, or a plurality of sensors, that detect the orientation of the body or torso, the acceleration, the velocity, the rotation and the position of the garment or person or the forces acting on the garment itself. The APG further comprises a logic controller that is capable of activating the air bag inflator should certain criteria be met or fall outside of an acceptable range. The logic controller is capable of distinguishing from a fall and other normal daily activities that can be mistakenly interpreted as a fall. The APG logic controller interprets electromagnetic inputs from the linked gyroscopic, position, velocity, or accelerometer devices. The air bag inflator is activated by the logic controller, deploying airbags or pockets on or in the garment that are rapidly and automatically expanded to provide energy dissipative or distributive padding to those areas of the body, of the person or animal wearing the garment, requiring protection from the fall or other impact. The garment further comprises an exterior surface that is capable of withstanding the local forces that might be experienced by the garment, including tension, compression, shear, abrasion, puncture, and the like.

There are many occasions when such an active protection garment is necessary, in addition to protection of elderly persons, active protective garments might also be valuable for persons involved in occupations or sports in which falls are a hazard. Examples where an APG garment would be useful include: people walking down the steps, people riding motorcycles, falling from standing, falling from a perch, skiers, snowboarders, skateboarders, surfers, football players, soccer players, rugby players, telephone linemen, building construction workers, members of the military, rock climbers, elderly people in nursing homes, falling from a moving vehicle such as a bicycle or open car or truck, and children at play. For many of the applications, the garment and its activation mechanism would be different. Variation in the protective elements of the active protective garment can be tailored to the specific activity or threat from which protection is required. A garment to protect an elderly person from a broken hip would be different from a garment to protect a bicyclist from cervical spine injury during a fall or collision because the forces, ballistics, kinematics, biomechanics, and regions to be protected are different. The principle of active protection is common among devices for all the aforementioned applications in that the APG detects body orientations, velocities, accelerations, rotations, and motions that are associated with an accidental fall and uses logic circuits to trigger deployment of personal airbags.

The active protection garment for an elderly person, can be a pair of shorts, or briefs, that are worn about the waist and extend downward to cover and provide active protection for the hips. The APG components can be built into baffles in the underwear or outerwear. These APG shorts can be underwear or undershorts so that a more stylish garment may be worn over top of the functional underwear. The APG shorts may comprise part of a garment that is worn as the outer layer of clothing. The APG shorts may have an elastic waistband that is easy to take on and take off. The leg openings may be close fitting, again for ease of the user. The APG shorts can be fabricated from two separate fabric layers of non-gas-porous material, such as, but not limited to, rip-stop nylon, polyester, Kevlar, polyolefin, ePTFE, and the like. The separate layers can be further subdivided into pockets or chambers that are isolated from each other. The fabric layers of the APG comprise regions of porosity to allow for breatheability.

Alternatively, the APG may enclose separate pockets of non-gas-permeable material that serve as the airbags. The pockets themselves may comprise airbags or may be simply fitted to accommodate a small, self-contained airbag and pressure source. The location, size and volume of the airbags are determined by the anatomic area to be protected. The size of the individual airbags is kept to a minimum to provide rapid, full inflation with a small amount of gas. Small individual airbags will limit the size and weight of the gas sources required for optimal inflation.

Isolated tubes, conduits, or other pathways connect the subdivided pockets or airbags to a single point. The single point connection or inflation port is fed by the output of the air bag inflator. A pressurized canister, filled with gas such as, but not limited to, $CO_2$, nitrogen, argon, helium, and the like is connected to the input of the air bag inflator. A selectively openable valve may be affixed to the exit of the canister or cylinder and the outlet of the valve may be sealed to tubes, conduits, manifolds, or baffles within the APG shorts. The selectively openable valve is controlled by the air bag inflator device, which is triggered by output from the fall-detecting sensors and logic circuitry. When no valve is present, air bag inflator is directly affixed to the tubes, conduits, manifolds, or baffles of the APG shorts for flow of gas therebetween. The gas is preferably inert and unable to oxidize or react with other substances. A controller is electrically connected to the air bag inflator. Force, motion, position, acceleration, or a combination thereof sensors are located in the waistband of the APG shorts and, optionally at a location in at least one of the legs. The sensors, can also be located remotely, on a wristwatch, on the back of the neck, or on a strap around the torso and remotely signal activation of the APG.

When the sensors detect the conditions of a fall in progress as evidenced by acceleration, distance, velocity, direction, discoordination, or a combination of parameters, etc., the controller sends a signal, by hardwire or electromagnetic radiation (e.q. radio waves, infra-red, microwave, etc.), to the logic controller. The logic controller sends an electrical or electromagnetic signal to the airbag inflator letting $CO_2$ (or other) gas move from the canister through the conduits to the subdivided chambers of the APG shorts. Alternatively, the logic controller may send the electromagnetic signal to the valve, causing it to open. The subdivided chambers or airbags inflate to a pre-specified pressure. The pressurized chambers provide additional padding around the hips to prevent bone fracture when the individual hits the ground or other surface. The multiple isolated chambers prevent unwanted redistribution of the pressure away from the impact site on the APG shorts. The APG is tailored to the anatomy of the site requiring protection. The garment may also be tailored to accept airbag elements placed in pockets designed for this purpose.

The biomechanics or ballistics of falling from standing height requires that the system react to deploy within 0.5 seconds or less. For example, in a directly vertical fall from standing, for a 5-foot tall person, the hips drop 2.5 feet, at the 32-ft/sec$^2$ acceleration due to gravity, before they hit ground in approximately 0.28 seconds. Other types of falls, including slips while walking, tripping, falling forward, or falling backward, may involve changes in verticality from the loss of balance to the impact. If the sensors detect an orientation, distance, acceleration, or direction that moves beyond programmed limits from vertical to horizontal too quickly or where the gravitational force on the sensors falls below programmed limits, the APG shorts are activated. Activation involves deployment or inflation of the airbags. Activation, deployment of the airbag or other barrier, must be complete within a faction of a second from the start time of the fall. The wearer might not want to wear the APG shorts on a roller coaster or other ride where such forces might occur and cause a false positive activation. Alternatively, a manual disarm switch may be provided for use in circumstances where the APG might deploy inappropriately or unnecessarily.

The algorithm for detection of an accidental fall could use any number of parameters to trigger inflation of the APG such as: 1) A rotation rate between sensors on the waistband or torso and at the bottom of the leg exceeding 45 degrees in 0.1 seconds would trigger activation of the inflation mechanism; 2) a nearly weightless condition for a period of 0.1 seconds would also trigger an inflation; or 3) lateral and vertical accelerations meeting certain parameters with respect to each other and with respect to normal values would trigger the inflation. Additional algorithms include velocity measurements where the vertical velocity is becoming increasingly negative (increasingly fast approaching the ground) and the horizontal velocity is increasingly positive. This scenario correlated with a vertical velocity in magnitude greater than negative 1 meter per second are strong indicators of a fall in progress and are distinguished from normal conditions such as sitting down, getting into a bathtub, putting on shoes, walking, etc. Another approach is to trigger the device based on velocity slope reversal such as when the vertical velocity falls outside a set range such as 1 meter per second and moves from positive to negative in a short period of time (usually less than 0.25 seconds).

Alternatively, a distance sensor using, for example ultrasound, microwave, radar, sonar, or infrared distance measurement would continuously ping the environment to determine the distance to objects such as the floor, a chair, etc. Integrals of the distance would be continuously calculated to determine velocities and integrals of the velocity would determine accelerations. Such distance sensors with their first order and time-differentiated measurements are used to calculate the presence of a fall in progress. Basic accelerometers can provide much of the needed information. Here, the nearly weightless condition would be, for example, an acceleration of less than ½ G, or 16 ft/sec$^2$. The inflation period occurs in 0.1 second or less. A lateral acceleration exceeding 0.5 g for a specific period of time would also trigger deployment or activation. The distance measuring system operates in conjunction with one or more accelerometers and can provide information relating to the occurrence of an actual fall in progress.

The relative position of the accelerometer devices may be tracked by the system. This can be achieved by keeping a record of location over time using a lookback algorithm. However stacking errors will render such a system difficult to accomplish. One possible method or system is to periodically re-calibrate position relative to an absolute location, position, or level plane. The plane is preferably defined in the right-left direction, anteriorposterior direction, north-south direction, and up-down direction. The re-calibration is significant to determine, for example when a wearer is standing up versus lying down or when a wearer is standing versus falling.

The sensors may comprise a plurality of accelerometers coupled to a plurality of primary position sensors. The accelerometers and position sensors are distributed over the person to be protected. One or more or all of these devices can be implantable but can also be made part of a garment or jewelry. Using transponder technology or RF receiver-transmitter technology, sensors without power supplies may be distributed around the patient. Energy is transmitted from a power source to transponders that are distributed at pre-determined locations on the body. The power is used to operate accelerometers and position sensors in sensor modules. The system can comprise a level that is affixed, removably or permanently, to the patient. The transponders periodically update their relative positions relative to each other and relative to level as determined by a leveling system. An external leveling system, on a walker, bed, or chair for example is suitable for providing the reference points needed to calibrate the system.

The supply of high pressure or compressed gas for the APG shorts can be derived from a plurality of distributed sources rather than a single source. This feature eliminates or minimizes the need for conduits, tubes, manifolds, or baffles in the shorts to conduct the gas from the source to the plurality of isolated chambers. A plurality of canisters or cylinders, filled with gas, can be distributed to empty into one or more, but not all, of the isolated chambers. The plurality of sources of gas improves the response time of the system so that inflation can occur more quickly than if the gas is forced to flow through tubes, manifolds, or conduits.

With the distributed gas source, multiple cylinders, filled with high pressure or compressed gas, are disposed within the APG shorts. Each gas cylinder has its own valve or airbag inflator. The airbag inflator is connected either directly by electrical wires or by electromagnetic waves to the logic controller and power supply.

Alternatively, one or more solid-state pyrotechnic devices with electrical air bag inflators can be allocated to each of the isolated chambers of the APG shorts. The electrical air bag inflators are connected to a central logic controller and power supply, which receives triggering information from the plurality of accelerometers and/or gyroscopes. The solid-state pyrotechnic inflators, or solid chemical inflators, utilize a fuel and an oxidizer to generate gas at a pre-determined rate. Stabilizers such as silicon dioxide are added to the material to control the rate of the reaction and prevent it from being too explosive. Examples of solid-state fuel/oxidizer mixture include, but are not limited to, sodium azide ($NaN_3$) with a potassium nitrate ($KNO_3$) oxidizer and gunpowder. These pyrotechnic devices can be made very small and light. They can be less than 1/10 the size and weight of a gas cartridge capable of the same performance. The amount of chemical can be carefully controlled to provide the exact amount of pressurization and volume to the APG shorts. Typical sodium azide pyrotechnic inflators use about 750 milliamps at around 12 Volts for ignition and completely outgas to pressurize the compartment in around 40 milliseconds (0.040 seconds). Lower power devices are preferable for this application and a 0.1 amp 3-volt system is preferable.

Alternatively with the pyrotechnic devices, a catalyst can be thrust into a small chamber filled with reagents that generate gas such as carbon dioxide. The catalyst can be inserted into the system by breaking a barrier between the catalyst and the reagents or it can be mechanically introduced by a small pyrotechnic charge, motor, or other source of force.

The distributed system can also comprise canisters that further comprise a reagent and a catalyst that generates foam that expands to fill the chamber of the APG.

Alternatively, the electrical connections between the logic controller and the airbag inflator or valve actuator can be made through electrical wires integrated into the fabric of the APG. The integrated wires are also appropriate for the connections between the logic controller and the power supply and between the logic controller and the plurality of accelerometers or gyroscopes. Such invisible wiring improves the appearance of the shorts, minimizes the bulk of the shorts, reduces the overall cost of manufacture, and improves the performance and reliability of the system. The connections between the logic controller and the airbag inflator or actuator for the valve can be made using electromagnetic waves such as, but not limited to, radio, microwave, infrared, and the like. Communications via electromagnetic waves or other wireless methods can be encoded, digitally or otherwise, to prevent spurious outside signals from inadvertently causing deployment of the airbags at the incorrect time. Wireless protocols such as those known as Bluetooth or PicoNet are appropriate for such short-range wireless protocols carrying digital signals.

The power supply for the APG is a battery or a capacitor. The battery can be a rechargeable battery comprising chemistries such as, but not limited to nickel cadmium, lithium ion, nickel metal hydride and the like. The battery may also be a non-rechargeable battery such as certain lithium chemistries and alkaline chemistries. A suitable battery is a 9 Volt radio battery, rechargeable or non-rechargeable. Batteries with lower voltages and output ratings may require the use of an optional capacitor, which is charged over time and discharged quickly to enable ignition of the solid fuel pressurization system or other pressurization system.

The APG can utilize a plurality of accelerometers to determine the status of the wearer. An example of an accelerometer suitable for such purpose is disclosed in U.S Pat. No. 5,345,824 to Sherman et al, the entire specification of which is incorporated herein by reference. The accelerometers should function in at least two orthogonal planes and at least two, and preferably three or more, such multi-directional accelerometers are used providing three orthogonal directions of acceleration detection and analysis. Each accelerometer measures along three orthogonal axes. Thus, velocity, distance, and acceleration are measured along with rotation rates, distances, and accelerations. Outputs from the accelerometers are monitored and algorithms including integration and derivation are performed to determine velocity and distance. Velocities in both the forward and negative direction are determined by calculating the derivative of the acceleration data over time and position information is obtainable by further taking the derivative of the velocity data over time. Accelerometers such as those manufactured by ST Microelectronics, Analog Devices, or Motorola are appropriate for this application. An accelerometer with a range of ±2 g is acceptable for this application. An accelerometer with a range of ±1 g is also acceptable and accelerometers with larger ranges might also work although they would have reduced resolution in the critical ±1 g range where most fall data occurs. A two-direction accelerometer is advantageous over a one-direction accelerometer and a three-direction accelerometer is most advantageous. Two such multi-direction accelerometers can be used and their outputs correlated to determine the event of a fall in progress.

The logic circuitry or computer onboard the APG will necessarily run a sophisticated program to continuously monitor sensor outputs, integrate or differentiate as necessary, and develop motion information. The system needs to integrate or differentiate the data, continuously track motion, and use a look-back function for periods on the order of 1 second to 10 minutes. The look-back function should last between 10 seconds and 60 seconds. During the look back period, the computer will evaluate motion and determine whether a fall is in progress as dictated by pre-set conditions or string of conditions or rules. The measured motions are continuously evaluated against the rules to determine whether or not a fall is in progress. Significant computational power including processor speeds and memory are required for such computations to be performed. For example, a 100 mHz or higher clock speed in the processor and memory of 128 megabyte or more is preferred. Sensing rates of 1,000 measurements per second for three accelerometers along three axes implies 9,000 measurements per second. Sixty seconds of data will require 60 times 9,000 or 540,000 measurements. The memory will require approximately 1 megabyte to hold 540,000 16-bit words. To obtain velocity and distance, another 2 megabyte of 16 bit words are required. Computational storage may require an additional 32 megabytes of memory. Therefore a system with approximately 48 to 64 megabytes of memory should be more than sufficient.

Alternatively, in the APG system, sensors can be located in or on the patient. The sensors are transponders or RF ID type devices. A transmitter transmits wireless signals at a certain frequency. The RF ID transponder receives the information and re-transmits at a new frequency. A sensor or sensors mounted on the patient determine the beat frequency between the transmitting and receiving transducers and calculates relative motion between the two transducers using Doppler shift methodology. This method can be used to determine the distance between a plurality of transducers affixed, removably or permanently, to the patient. The RF ID device, can also use microwave, RF, ultrasound, sound, or simple electrical signals transmittable through body tissue, and the like.

The APG system comprises algorithms to understand whether the person is walking, standing, sitting, lying down, or the like. These algorithms are used to supplement and real-time and/or look-back motion data to determine whether a fall-in-progress is occurring.

The APG can also comprise distance sensors such as those that use ultrasonic signals, sonar, microwave, radar, or the like, to determine the distance to an object. Should the APG distance sensor determine that the distance to an object is too close, or closing too rapidly, that information can be used in determination of whether or not to activate the protection devices in the APG. The distance detector optionally comprises logic circuitry to discriminate between hard and soft surfaces such as between a floor and a couch or chair seat. In addition, the rate of closure as well as the accelerations of closure are optionally analyzed and used to determine whether or not to activate the APG.

The APG can comprise sensors that work in conjunction with room or building mounted transmitters, transponders, sensors, or the like to determine position within the room or even outdoors. These devices work on principles similar to GPS except at much closer range and with much higher resolution. Should the APG and room mounted sensors determine that the person is too close to the floor, or falling to rapidly, the APG is activated.

The APG can comprise rotational acceleration sensors such as the type manufactured by ST Microelectronics. Such rotational acceleration sensors are capable of measuring rotational acceleration. The information can be derived over time to obtain rotational velocity and derived again over time to obtain rotation distance or angle. Such rotational acceleration information can be used alone or in conjunction with other accelerometers or distance sensors to detect a fall in progress. A rotational accelerometer system has the potential to eliminate the need for one or more linear accelerometers in the entire system, thus providing for more simplicity and cost-savings.

The APG can also comprise one or more gyroscopes of the type disclosed in U.S. Pat. No. 6,470,748 to Geen, the entire specification of which is incorporated herein by reference. The gyroscopes can be used alone, or in conjunction with the accelerometers.

The APG can also comprise a link to a Personal Emergency Locator System (PELS) of the type disclosed in U.S. provisional patent application No. 60/419,510 to Buckman et al., the entire specification of which is incorporated herein by reference. Activation of the APG triggers a signal to a PELS system to call emergency services or other support personnel to assist the wearer.

The PELS, described above, can further comprise internal detection circuitry to sense the discharge of a defibrillator. Defibrillator outputs typically are either monophasic or biphasic signals that have characteristic signatures. A separate piece of jewelry such as a wristband or chest strap further comprising electrodes or other voltage or current sensors detects the firing of an internal (ICD) defibrillator or an external defibrillator. The isolated PELS receives signals from the Global Positioning System (GPS) satellites and its internal clock and decodes the detected waveform as a defibrillator countershock. A wireless telephone call is made via cell phone or other stratagems to verbally notify emergency personnel such as those supporting the 911 emergency network that a defibrillator countershock event has occurred at the determined GPS coordinates and time and that emergency personnel should be sent to attend the wearer. In this capacity, the person is protected against cardiac arrest as-well as from falling.

Using the same principles, other types of protective garments can be fabricated. Each garment is specifically tailored to protect against specific incidents or the garments can be tailored to meet a wide range of potential and unforeseen incidents. Examples of such garments include a specially designed collar on a coat, shirt, vest, or other garment that inflates and expands upwards and radially to protect and support the neck or the head. The expandable collar can be completely hidden inside the collar of a standard appearing coat such as a bomber jacket or ski jacket. Other regions of the coat or vest can be made to form armor and/or active airbag protection against impact. For example, specific torso regions of the coat, undershirt, shirt, or vest or the arms of the coat or shirt can be made with chambers that automatically fill with pressurized gas to protect the back, the abdomen, or the arms. The APG coat, APG shirt, or APG vest inflation, if so configured for full or partial torso inflation, serves the double benefit of protecting against impact but also becoming rigid and protecting against bending stresses that could cause spinal cord damage or damage to the vertebrae.

APG trousers can be fabricated comprising the basic elements of the APG shorts, e.g. sensors, logic, pockets, airbag, pressure source, etc., but including longer leg regions to protect the complete lower extremity or a portion of the legs. Such APG pants or trousers optionally include cuffs to extend and protect the foot following activation. The APG trousers necessarily meet requirements for style, comfort, ease of taking on and off, and wearability.

The APG coat, vest, shirt, or shorts can further comprise an outer layer that is resistant to penetration or puncture such as is derived from woven Kevlar fabrics with suitable reinforcement.

The APG can comprise a helmet or hat with airbags that expand downward toward the shoulders from the bottom of the helmet or hat. The airbags serve to support and stabilize the neck to minimize the risk of neck injury during a fall. While helmets protect the head from impact, they do not adequately protect the neck from fracture, excessive bending, compression or ligamentous damage. The airbag or APG collar on the bottom of the hat or helmet can support the neck to minimize torsion, compressive, or bending stresses that can cause fracture and protect the neck from impact stresses.

For each type of garment, the airbags are manufactured either as part of the garment or they are added to the garment by placing them into pockets (like a pita pocket) on the garment that are made for the purpose of holding the airbags. The airbags are held in the pockets using fasteners such as, but not limited to, snaps, Velcro, zippers, buttons, and the like. The garment can be cleaned more easily after the airbags and certain of the associated components are removed from the garment. The garment is also more breatheable because only a portion of the surface is covered by gas impermeable compartments or airbags. The airbags, in a fully isolated position, each contain activation or inflation, logic and sensing componentry. The airbags communicate with one another over short-range wireless, or wire, communications protocols to provide the required information to detect a fall and react thereto. Isolated airbags are beneficial because the volume requirements are reduced over a bag that fully encompasses the expanse of the garment.

The airbags or compartments of the APG are made in a variety of shapes and sizes. Typical beneficial shapes for a pair of APG shorts includes, but is not limited to, "H", shapes, "C" shapes, "T" shapes, "Y" shapes, "I" shapes, "O" shapes, and the like. These discreet shapes allow for protection over the critical parts of the body, such as the pelvis and the upper femur, without padding those areas that are not likely to hit during a fall or which are already adequately padded, and with a minimal volume encompassed by the compartment or airbag.

Where the airbag fits into a pocket on the garment, the airbag may be made to be rolled or folded so as to occupy less than a full portion of the pocket. Thus, the garment may be made to breathe through much or most of its surface area. The airbag will unfurl, unroll, unfold, expand, or enlarge to fill the pocket following activation and inflation.

A plurality of accelerometers or other sensors can be distributed on the patient by either implantation, or by adhesive attachment to the patient via a patch or patches. The implantation or adhesive attachment to the patient provides reliable, repeatable location for the sensors that can be relied on to generate data that is useable by the logic controller to detect a fall in progress. Sensors that are not well affixed to the patient, such as those affixed to garments or jewelry, will be less well attached to the patient so positioning is less accurate and more subject to errors in measurement or inappropriate locating by the patient. The logic circuitry generally requires exacting knowledge of the positioning of the sensors to determine the interrelationship between the measurements that are taken. The logic circuitry integrates or derivates the data from the plurality of sensors, preferably three or more three-dimensional sensors that can measure motion in three directions and three axes of rotation, relative to time. Rotation rates of accelerometers requires that acceleration data be derived to determine velocity and that the moment arm between the two sensors be known with substantial precision.

The APG can comprise elements in a helmet at or near the base of the helmet. Additional elements can be comprised by the top region of a shirt, coat, or upper torso garment. Shoulder pads, such as those found in football uniforms are ideal upper torso garments to carry the APG. The APG senses extreme rotation, hyperextension, lateral flexion, or hyperflexion of the neck. A restraining device such as an airbag is deployed upon generation of an activation signal. The restraining device extends downward from the helmet and/or upward from the upper torso garment. The restraining device, under pressure, exerts forces to resist extension, flexion, and compression of the neck. Applications include football, motorcycle riding, skiing, snowboarding, equestrian sports, surfing, skateboarding, industrial applications, skydiving, military applications, and the like. In the case of a helmet-mounted device, the protective mechanism deploys downward and exerts pressure on the shoulders of the wearer. In the case of an upper torso garment mounted device, the protective mechanism deploys upward from a collar to surround the neck and protect against undue flexion or extension.

The APG can comprise an on-off switch to disable activation during periods of unwanted functionality, such as during a ride in an amusement park, using a toilet, or when the APG is removed and thrown into the corner of the room. The on-off switch may, optionally or additionally, comprise a thermal sensor such as a thermister or a thermocouple that detects the heat of the patient's body and disables the APG when it detects temperatures not consistent with proximity to the patient's body (approximately 37 degrees centigrade less a couple of degrees due to skin losses and insulation effects of fabrics). The on-off switch may be an automatic device triggered by tension of a waistband or other internal strap or elastic member. The APG protection mechanism can be triggered by receipt of signals from a sensor that monitors physiological information such as ECG, EEG, EMG, pulmonary function, or the like. The APG would offer further protection to a person who might lose consciousness or become convulsive and lose the ability to stand or remain upright.

Sensors for muscle stimulation can monitor the electromyelogram or EMG output of certain muscles. Those muscles that would be triggered to react during a fall such as those in the arms and shoulder region are candidates for such monitoring. The EMG data, alone, may be used to trigger the activation of protective devices or it may be used in conjunction with a plurality of accelerometers and/or distance sensors. The logic circuitry analyzes, integrates and derivates the data to make the determination of whether or not to activate the protective device.

One or more strain gauge devices may be embedded in a garment. These strain gauges detect joint flexion and by monitoring their output, information leading to an activation event or supporting an activation event can be obtained. Such strain gauges are resistive elements that, upon elongation, increase resistivity. Such elongation is made to occur when a muscle is flexed or a joint is bent, causing the fabric of the garment to be stretched or bent. The change in resistivity is used in a Wheatstone bridge circuit to cause changes in electrical current to an amplifier, the output of which is fed through an Analog to Digital converter and into the logic circuitry for analysis.

BRIEF DESCRIPTION OF THE DRAWINGS

FIG. 4 illustrates a front view of a pair of APG shorts being worn by an individual;

FIG. 5A illustrates a side view of a pair of APG shorts on a standing individual;

FIG. 5B illustrates a pair of APG shorts, which have activated because they are being worn by an individual who has begun falling;

FIG. 5C illustrates a pair of APG shorts being worn by an individual who has fallen and whose hip has struck the ground;

FIG. 7A illustrates an APG collar on a jacket prior to activation;

FIG. 7B illustrates an APG collar on a jacket following activation;

FIG. 8A illustrates an APG jacket prior to activation, according to aspects of an embodiment of the invention;

FIG. 8B illustrates an APG jacket after activation;

FIG. 9A illustrates a pair of APG trousers prior to activation.;

FIG. 9B illustrates a pair of APG trousers following activation; and

DETAILED DESCRIPTION OF THE INVENTIONS

Figure 1A:
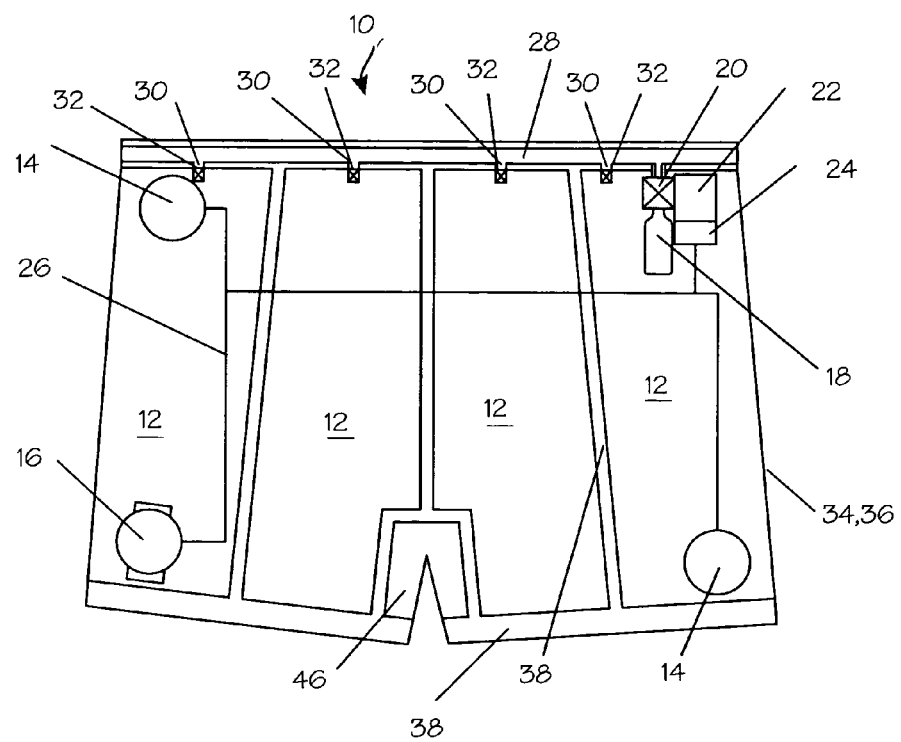
FIG. 1A illustrates a pair of deflated APG shorts.

FIG. 1A illustrates pair of deflated APG shorts 10. The APG shorts 10 comprise a plurality of chambers 12, a plurality of accelerometers 14, one or more optional gyroscope 16, a high pressure or compressed source of gas 18, a logic controller 22, a battery 24, an electrical bus 26, a manifold 28, a plurality of chamber inlet ports 30, and a plurality of one-way valves 32. The APG shorts can optionally have an actuator valve 20. The chambers 12 can further comprise two layers of gas impermeable wall 34 and 36, a plurality of seals 38 and one or more non-inflatable regions 46.

The chambers 12 are isolated regions within the APG shorts 10 that cushion the impact between the wearer and the object being hit by the wearer. The chambers 12 are connected to the high pressure or compressed gas source 18 by a manifold 28. A valve 20 may be contained to control and enable the gas flow from the compressed gas source 18 to the manifold 28. The entry to each chamber 12 is a chamber inlet port 30. Each chamber inlet port 30 may be connected to the manifold 28 by a one-way valve 32. The valve 20 is opened or closed by the logic controller 22, which is further powered by a power supply 24. Inputs to the logic controller 22 are electrically connected to a plurality of accelerometers 14 and/or a plurality of gyroscopes 16 by an electrical bus 26. The APG short also comprise a plurality of non-inflatable regions 46. All components are affixed to the APG shorts 10.

The chambers 12 can comprise cornstarch, talc or other dry lubricant to prevent blocking or wall adherence that could prevent proper inflation when desired.

The high pressure or compressed gas source 18 can be a canister of gas such as, but not limited to, carbon dioxide, nitrous oxide, nitrogen, argon, or the like. The high pressure or compressed gas source 18 may also be a pyrotechnic device or a catalytic device that, once activated by the air bag inflator, generates a gas such as nitrogen, carbon dioxide or other non-flammable material, that expands under great pressure to fill the manifold 28 and the chambers 12. A typical solid-state gas source comprises sodium azide ($NaN_3$) with a potassium nitrate ($KNO_3$) oxidizer encapsulated within a filter and containment chamber with holes through which gas can escape. The device further comprises an electrical air bag inflator that causes activation when the proper electrical signal is applied to the inflator. Typical devices of this type use 12 Volts DC and 750 milliamps to activate the inflator although lower energy inflators are possible and desirable. Such gas sources 18 are capable of fully outgassing beginning around 5 milliseconds from the presence of the electrical signal in the inflator and completely outgassing in times as short as 40 milliseconds or less. Longer outgassing times, up to 100 or 200 milliseconds, may be appropriate for the application of the Active Protective Garment. Very fast outgassing devices have uses in systems where the fall is detected in its terminal stages or even after impact when a velocity reversal occurs. Extremely fast inflation at that point may still distribute forces and prevent injury to the wearer.

When the Active Protective Garment contains a valve, 20 the valve is activated either by motor or explosively operated such that once a triggering signal is received from the logic controller 22, the valve opens within less than 0.05 seconds and preferably within less than 0.01 seconds. The high-speed opening mechanism of the valve 20 is either fusible or motor-driven. The valve 20 optionally comprises a pressure regulator to ensure that the proper pressure is applied to the manifold 28 and, subsequently, the chambers 12. When the valve is not present, the air bag inflator deploys within these same time limits.

The one-way valves 32 are passive valves that permit gas to enter the chamber inlet ports 30 but not to escape in a retrograde direction. Valves of this type include, but are not limited to, duck bill valves.

One or more non-inflatable regions 46 are located in areas that normally would not require protection and which, if explosively inflated might cause damage or discomfort to the person wearing the APG shorts 10. Such areas where a non-inflatable region 46 is appropriate include the crotch area. Selective areas of non-activation such as the non-inflatable region 46 are preferably in areas that would not normally receive an impact load during a fall.

The electrical bus 26 includes all electrical wiring between the sensors, including the gyroscopes 16 and the accelerometers 14 and the logic controller 22. The electrical bus 26 is also comprised within the logic controller 22 interconnecting all components electrically. The electrical bus 26 also connects the logic controller 22 and the air bag inflator or the valve 20, thus sending a signal to open at the appropriate time.

Figure 1B:
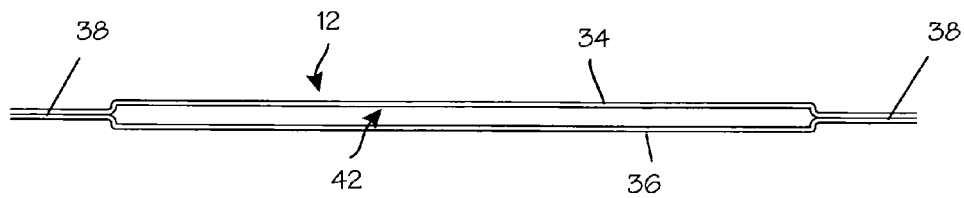
FIG. 1B illustrates a cross-sectional view of one of the deflated chambers of the APG shorts.

FIG. 1B illustrates a cross-sectional view of a chamber 12 of the deflated APG shorts 10. The chamber 12 further comprises an inner wall 34 and an outer wall 36, seals 38, and an interior volume or space 42. Suitable materials for the inner wall 34 and the outer wall 36 include, but are not limited to, polyester (PET), polyimide, polyurethane, polytetrafluoroethylene (PTFE), nylon, Dacron, Kevlar, copolymers of the aforementioned, rip-stop nylon, cotton, and the like. The inner wall 34 and the outer wall 36 may be of different materials or they may be of the same materials. The material is preferably woven to maximize strength although knitting or other fabric forming processes are also acceptable. Strengthening fibers fabricated from Kevlar or polyester, for example, may be used in conjunction with weaker materials to form a barrier cloth that is impermeable to gas but also has reinforcing strands. Impermeability may be achieved by coating a woven or knitted fabric with membranous materials such as polyurethane or PTFE. Alternatively, the entire wall 34 and 36 can be fabricated from polymeric sheet that is not woven or reinforced but is homogeneous.

Figure 2A:
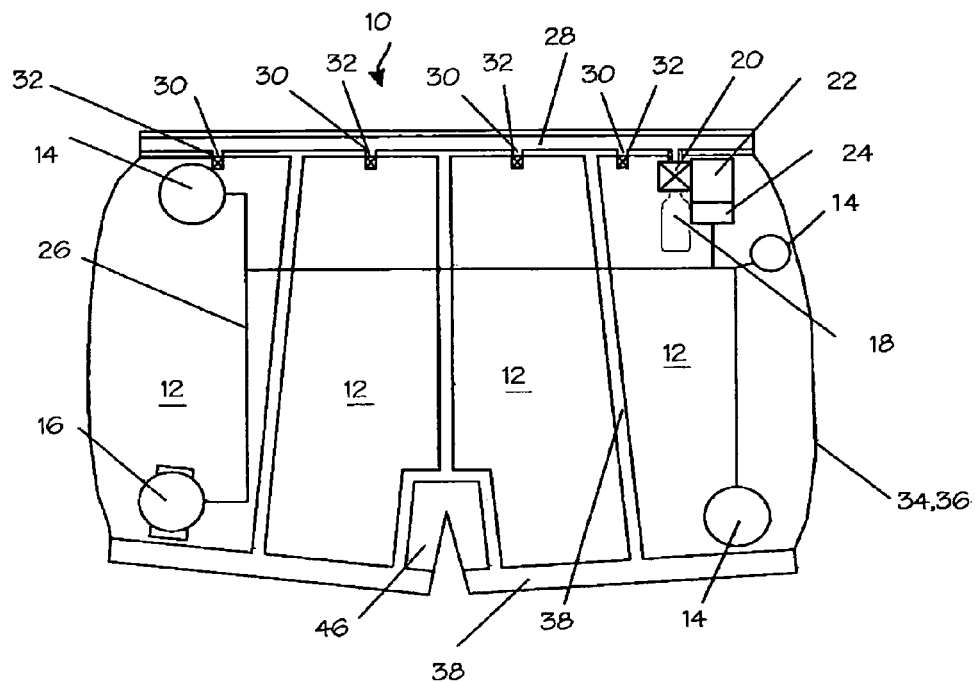
FIG. 2A illustrates a pair of APG shorts following activation.

FIG. 2A illustrates a pair of APG shorts 10 following activation. Referring to FIGS. 2A and 1B, the plurality of chambers 12 have become filled with pressurized gas and bulge outward to form a padded structure. Any amount of pressure generated within the interior volume 42 of the chambers 12 will provide some protection for the wearer, although sufficient pressure to prevent collapse of the exterior wall 36 against the interior wall 34 is preferable. For example, a 200-pound person resting on a 12-inch by 12-inch area or 1-foot square would require 1.39-pounds per square inch (PSI) internal pressure to support the weight. The same two hundred pound person falling from 2.5 feet would have an impact velocity of 8-ft/sec and exert a force greater than 200-lb due to their momentum. If they decelerated to a stop in 0.05 seconds when they hit the ground, the net force would equal 1000 pounds. Thus, the APG shorts require at least 6.94-pounds per square inch (PSI) to cushion the fall over a 1-square foot (144 square inch) area, under this scenario.

Figure 2B:
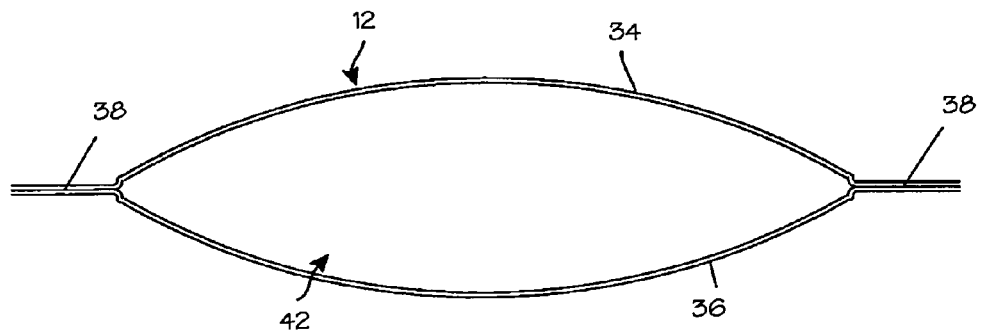
FIG. 2B illustrates a cross-sectional view of a chamber of the APG shorts following activation.

FIG. 2B illustrates a cross-sectional view of a chamber 12 of the APG shorts 10 following activation. The chamber 12 further comprises the inner layer 34 and the outer layer 36, a plurality of seals 38 and an inner volume 42. The chamber 12 has become inflated with pressurized gas and forms a padded structure to protect the wearer. The internal pressure within the internal volume 42 of the chamber 12 is sufficient to prevent collapse of the inner volume 42 between the inner layer 34 and the outer layer 36 of the chamber 12. The width of the seals 38 is sufficient to provide a strong bond so that the two layers 34 and 36 do not become separated by the tensile forces created by the pressurized internal volume 42. The width of the seals 38 is not so wide that the person wearing the APG shorts 10 would be unprotected if they fell on the seal 38. The seal 38 can be a heat seal created by compression of the two fabric layers 34 and 36 at specified temperatures, pressures and times such as to form a strong weld between the two layers 34 and 36 of material. Alternatively, each chamber 12 can be separate from the next and the separation wall does not comprise a seal 38.

Figure 3A:
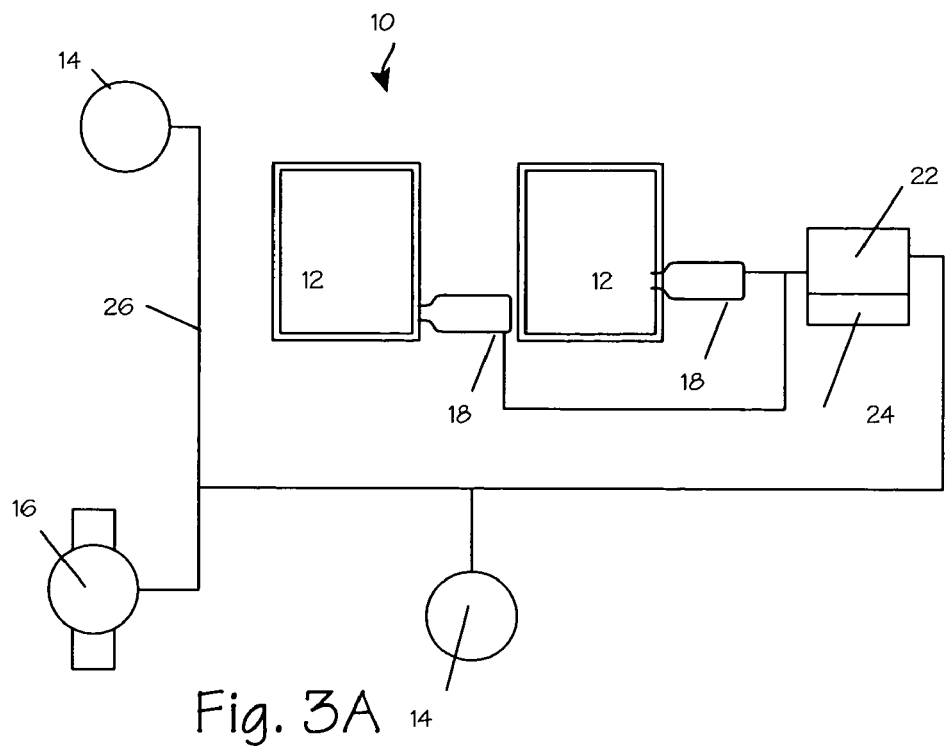
FIG. 3A illustrates a block diagram of the components of a pair of the APG shorts.

FIG. 3A illustrates a block diagram of the systems comprising the APG shorts. The APG shorts comprise a plurality of cushioning chambers 12, one or more accelerometers 14, one or more gyroscopes 16, a high pressured or compressed gas source 18, a logic controller 22, and a power supply 24.

The logic controller 22 is a computer and controls all aspects of function of the device from acquiring information from the gyroscopes 16 and the accelerometers 14 to determining whether an actuation condition exists to the airbag inflator (not shown) to inflate the chambers 12 to providing notification of the status of the power supply 24 or controller 22 malfunction. The software (not shown) controls the function of the logic controller 22.

The power supply 24 can be a battery system powered by chemistries such as, but not limited to, lithium ion, nickel metal hydride, nickel cadmium, alkaline, lead-acid, and the like. The power supply 24 provides electrical power at the correct voltage and current to the electrical components of the APG shorts 10. The power supply 24, optionally further comprises a connection to either 110 VAC or 240 VAC power and serves as a charger for the battery, if appropriate.

The accelerometers 14 can be strain gauge devices that suspend a weight on one or more strain gauges. The strain gauges operate within a Wheatstone bridge signal conditioning circuit to cause voltage or current changes in the circuit proportional to the stress on the accelerometer 14. Strains and stresses in multiple directions may be measured using a plurality of these strain gauges. The strain gauge, signal conditioners, amplifiers and other required components may be comprised within a single monolithic structure for manufacturability, small size, low cost, and reliability. The accelerometers 14 may be distance or position sensors such as those employing ultrasonic acoustic waves, radar, microwave, infrared, or other methods to determine distance between the sensor and the ground or other object. Differentiation of the signal provides velocity information and further differentiation provides acceleration information. The velocity, distance, and acceleration information can be correlated to signal a fall in progress and activate the APG shorts 10.

The accelerometer 14 can be an ST Microelectronics LIS3L02. This device is available as either an analog or digital output device capable of measuring acceleration along three orthogonal axes. It is a micro-electromechanical system (MEMS) based chip that requires support circuitry including power supply, timing, and output circuitry.

The gyroscope 16 may be a ball or sphere suspended concentrically within a sphere. The outer sphere is affixed permanently to the APG shorts 10. The inner sphere is magnetically suspended within the outer sphere. The inner sphere is weighted so that slow motions of the outer sphere move the inner sphere in a 1:1 ratio. Fast motions of the outer sphere exceed the magnetic attraction between the two spheres and the inner sphere rotationally displaces relative to the outer sphere. Such rotational displacement is detected by changes in the magnetic field, electric field directed toward a portion of the inner sphere, etc. Rotational displacements sufficient to announce a fall in progress causes the logic controller 22 to send a opening command to the airbag inflator. Standard gyroscopes using spinning tops or other stabilization systems are acceptable for this use but require higher power drain and are more prone to reliability problems.

The gyroscope 16 can be replaced by one or more rotational accelerometers. Each rotational accelerometer can measure rotational acceleration about three axes, X, Y and Z. The rotational accelerometer, such as the one manufactured by ST Microelectronics is capable of providing rotational acceleration information. Taking the derivative of the acceleration over time results in the rotational velocity. A single-axis rotational accelerometer is the ST Microelectronics MEMS-based LIS3L02, an analog output accelerometer capable of performing the tasks required for this application. Support circuitry including memory, Analog to Digital conversion, clock, power, and the like are required for such a device. Taking a second derivative over time of the rotational velocity data will yield rotational displacement, angle, or distance.

Figure 3B:
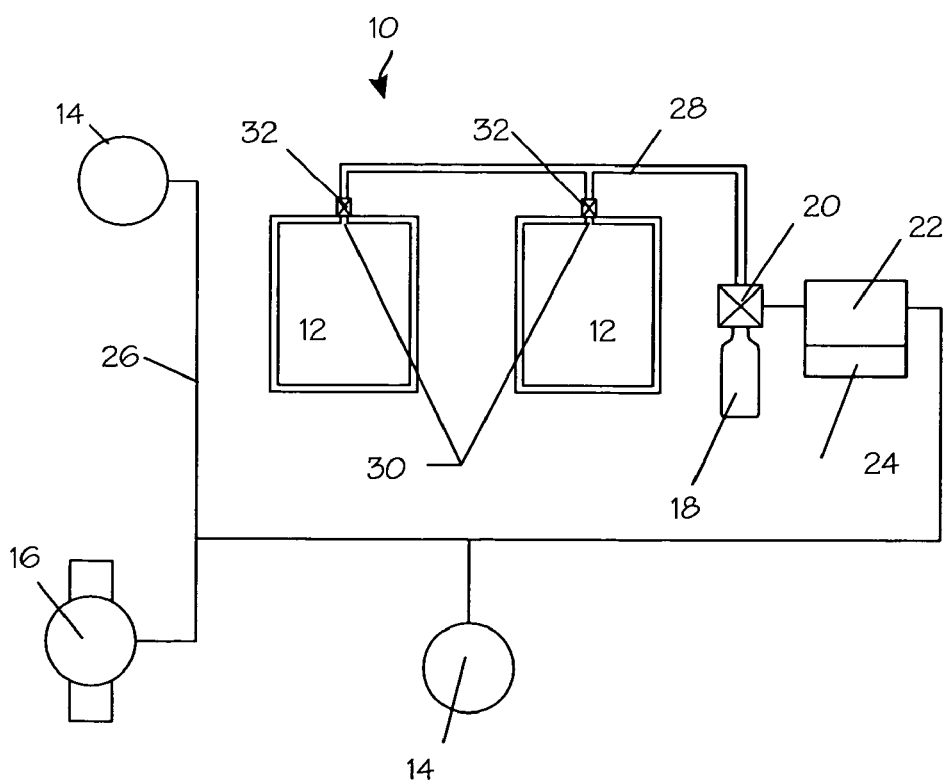
FIG. 3B illustrates another block diagram of the components of a pair of the APG shorts with actuator valves.

FIG. 3B illustrates another block diagram of the components of a pair of the APG shorts with actuator valves. The APG shorts comprise a plurality of cushioning chambers 12, one or more accelerometers 14, one or more gyroscopes 16, a high pressured or compressed gas source 18, an actuable gas valve 20, a logic controller 22, a power supply 24, an electrical bus 26, a gas manifold 28, a plurality of chamber ports 30, and a plurality of one-way valves 32.

The logic controller 22 is a computer and controls all aspects of function of the device from acquiring information from the gyroscopes 16 and the accelerometers 14 to determining whether an actuation condition exists to activating the valve 20 to inflate the chambers 12 to providing notification of the status of the power supply 24 or controller 22 malfunction. The software (not shown) controls the function of the logic controller 22.

The actuable gas valve 20 is motor operated, or opened by melting, moving, or dissolution of a plug. The melting, moving, or dissolution of the plug can be accomplished using electrical energy delivered from the power supply 24 and controlled by the logic controller 22 and delivered to the actuable gas valve 20 by the electrical bus 26. The valve 20 can be a ball valve, erodeable membrane, needle valve, gate valve, or any other suitable valve that can be fully or partially opened at high speed when activation occurs.

FIG. 4 illustrates a front view of a person 44 wearing the APG shorts 10. The APG shorts 10 are deflated in this illustration. The APG shorts 10 further comprise a plurality of separate inflatable chambers 12, one or more accelerometers 14, one or more gyroscopes 16, a high pressure or compressed gas source 18, an actuable gas valve 20, a logic controller 22, a power supply 24, an electrical bus 26 and one or more non-inflatable regions 46. The APG shorts 10 cover the pelvis, hips and upper femur of the person 44. The non-inflatable region 46 shown in FIG. 4 is in the area of the crotch where high-speed inflation could cause damage to genital organs. A falling person would not normally need protection at the front of the garment in the crotch area because this is an area which would not receive any impact from the most probable types of fall.

FIG. 5A illustrates a side view of a person wearing the APG shorts 10. The person 44 is standing in this illustration. Outer clothing is not shown but could be worn over the APG shorts 10.

FIG. 5B illustrates a side view of a person 44 wearing a pair of APG shorts 10. The person 44 in this illustration has slipped from a standing position and is in the process of falling. The APG shorts 10 have detected that an unusually high rotation rate is occurring and that gravitational acceleration has suddenly diminished more than in half. As a result of this information, the APG shorts 10 are in the process of inflating.

FIG. 5C illustrates a side view of a person 44 wearing a pair of APG shorts 10. The person has completely fallen and has landed on the ground with the greatest impact being absorbed by the buttocks and hip area. The APG shorts 10 are fully inflated to their operational pressure. The inflated APG shorts 10 prevent direct impact between the person's 44 hip or pelvis and the ground. A fractured pelvis is avoided in this circumstance. The entire fall takes place in approximately 0.25 seconds.

Figure 6:
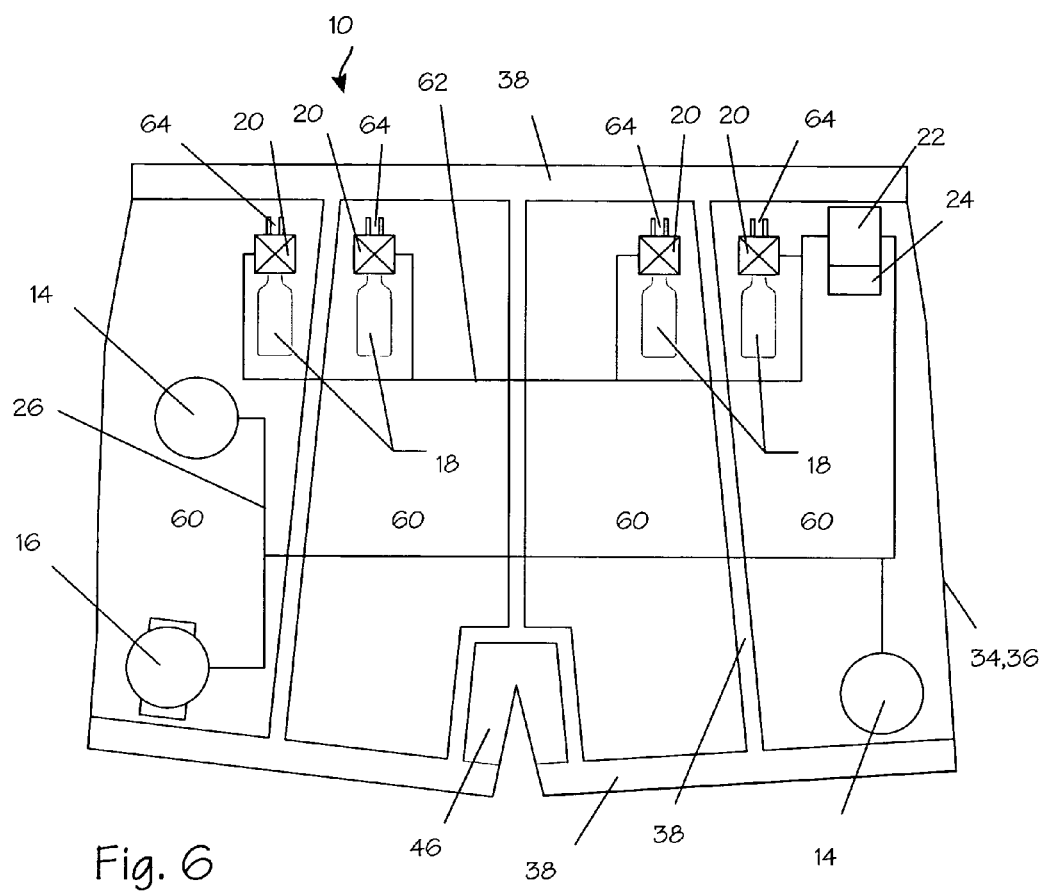
FIG. 6 illustrates a pair of APG shorts with distributed activation mechanisms.

FIG. 6 illustrates a pair of APG shorts 10 comprising a plurality of totally isolated or separated inflatable compartments 60, a plurality of sources of high pressure or compressed gas 18, a plurality of actuable gas valves 20, a plurality of gas vents 64, a system electrical bus 26, a system electrical output bus 62, a logic controller 22, a power supply 24, an inner fabric layer 34, an outer fabric layer 36, one or more accelerometers 14, one or more optional gyroscopes 16. The separate inflatable compartments 60 may be comprised of the inner gas impermeable fabric layer 34, the outer gas impermeable fabric layer 36 and a plurality of gas impermeable seals 38.

Referring to FIG. 6 and FIG. 1, the inflatable compartments 60, in FIG. 6, differ from the inflatable compartments 12 of FIG. 1 in that they are totally isolated and do not have the manifolds 28 or other passageways leading from the compressed gas source 18 to the compartment 60. The reaction time of the device shown in FIG. 6 is much quicker than that of the device of FIG. 1 in that the gas does not have to travel through tubes or passageways to reach a remote chamber 12. Instead, the gas is vented directly into the chamber 60. A plurality of airbag inflators are required, one for each gas source 18. The triggering energy for the airbag inflators is routed through the electrical output bus 62. The logic controller 22, the power supply 24, the accelerometers 14, the gyroscopes 16 and the rest of the system bus 26 are as described as in FIG. 1.

Alternatively, the device as illustrated in FIG. 6 may have a high pressure or compressed gas source 18 that is a solid or liquid material that is catalytically or pyrotechnically made to undergo a reaction, such as oxidation, that releases the correct amount of gas into the compartment 60 required to develop the specified pressure. Such pyrotechnic or catalytic devices have the property of being much smaller and lighter than a compressed gas canister and would not be visible, protrusive, or obtrusive.

The plurality of isolated chambers 60 are especially advantageous for a large APG garment such as a coat or trousers. It is not as necessary for a small garment such as a collar or a pair of shorts. It is still advantageous, for reasons of bulk and accelerated activation times, to use distributed inflation systems as described in FIG. 6 in small garments.

FIG. 7A illustrates an active protective garment in the configuration of an APG collar 70. The APG collar 70 is permanently affixed or integral to a standard jacket, coat, or vest, or the APG collar can be removably affixed to the jacket, coat, or vest. The APG collar 70, shown in FIG. 7A, is in its deflated, unactivated state. Referring to FIGS. 1A and 7A, the APG collar 70 comprises all the components of the APG shorts 10 but is specifically configured to protect the neck and at least part of the head of the person 44 wearing the APG collar 70. While the APG collar 70 may only need one inflatable chamber of compartment 12, it may have a plurality of such chambers 12 to improve pressure distribution throughout the APG collar 70 once activated.

FIG. 7B illustrates the APG collar 70 following activation. The APG collar 70 has activated because the person 44 wearing the APG collar 70 has begun to fall. Rotational and acceleration sensors in the APG collar 70 have determined that a fall is in progress and the logic controller has sent a signal to open the valve or release the airbag inflator to the compressed gas canister so that the compartments 12 fill to the pre-determined pressure. The APG collar 70 has expanded upward to protect the back of the head, the side of the head, and the neck from impact. In addition, the APG collar 70 provides stiffness to the neck and head to minimize the risk of cervical spinal injuries by preventing torsional stress to the upper spine. The APG collar 70 expands upward under the chin and, in conjunction with the rear and side head supports, keep the neck straight and aligned during an impact.

The face may be protected by a compartment 12 of the APG collar 70 that expands upward at the front of the head. Alternatively, in the APG collar 70, a compartment may be formed inward over the top of the head to provide protection to the top of the head.

A compartment of the APG collar 70 may extend downward along the spine to provide protection and stiffening to the spine during an impact, thus reducing the chance of or extent of spinal injury.

Such an APG collar 70 is a useful adjunct for persons riding bicycles or motorcycles or a person engaging in sports such as skiing, skateboarding, water skiing, snowboarding, and the like. Often participants in these activities prefer not to wear head protection because of style or comfort reasons and the APG collar 70 will still provide these people with impact protection. For these sporting applications, internal pressures and times to activation may need to differ from those when simply falling. Reaction times may need to be on the order of an air bag in a car. Sophisticated algorithms will be required in the logic controller to distinguish between a crash event and normal occurrences during some of these activities.

FIG. 8A illustrates a deflated APG jacket 80 being worn by an individual 44. The APG jacket 80 is normal in appearance and can be styled to match any trend or garment design. This APG jacket 80 does not further comprise an APG collar 70 as described in FIGS. 7A and 7B but such an APG collar 70 may be comprised by the APG jacket 80. Referring to FIGS. 1A and 8A, the APG jacket comprises all components specified for the APG shorts 10 of FIG. 1A. Referring to FIG. 7B and 8B, the operational parameters for the APG jacket 80 are more similar to those for the APG collar 70 than the APG shorts 10 because of high speeds and occasional low gravity events that might be encountered during the activities specified for the APG collar 70.

FIG. 8B illustrates the APG jacket 80 following activation on a person 44 who is falling. The APG jacket 80 has a plurality of compartments 12 that have inflated and will continue to-inflate to the specified pressure prior to the person 44 hitting the ground. The APG jacket 80 further comprises arm compartments 82 that have also inflated to protect the wearer 44 from arm impact and potential broken bones.

The APG jacket 80 may be configured as a shirt or undershirt that is completely hidden under outer layers of clothing.

FIG. 9A illustrates a pair of APG pants 90 being worn by a standing individual 44. Referring to FIGS. 9A and 1A, the APG pants 90 comprise all the elements or components of the APG shorts 10. A greater number of chambers 12 are required for the APG pants 90.

FIG. 9B illustrates the pair of APG pants 90 following activation on a person 44 who is falling. The APG pants 90 have a plurality of compartments 12 that have inflated and will continue to inflate to the specified pressure prior to the person 44 hitting the ground. The APG pants 90 may further comprise a compartment 12 that expands upward from the waist to protect the back and abdomen of the person 44. Such back and abdominal protection protects from impacts and also from torsional stresses that could cause strained back or abdominal muscles or ligaments. The control componentry of the APG pants 90 is affixed to the belt area of the APG pants 90 to maximize mobility, although one or more motion sensors may be placed further down the leg.

The APG pants 90 may be configured as underpants or an undergarment that is worn completely hidden beneath outer layers of clothing.

The material of the garment may be fabricated from fibers that are highly flexible in their unactivated state. Following activation, these fibers become more rigid and provide additional impact, penetration, and skid protection. Such materials are especially useful for motorcycle and bicycle riders that become abraded from falling. Nitinol fibers may be incorporated into the weave of the fabric of the APG garment. When activated, the nitinol is electrically or resistively heated to cause a phase transformation from a martensitic to an austenitic state. The nitinol fibers shorten to tighten up the weave or they pull the weave at a bias to cause the weave to become stiffer. Ohmic or electrical resistive heating of nitinol requires very little time and the response time is less than 1/100 second.

The nitinol shape-memory elements may be comprised of nanofabricated or micromachined into the cloth of the garment. Activation of the microscopic nitinol shape-memory elements by applying electricity to the elements, causes them to change shape to stiffen the fabric or cloth of the garment.

Fibers may be extended to project outward from the outer surface of the APG garment. The fibers, like hairs, serve the purpose of creating a slip layer and minimizing shear on the surface of the fabric, thus minimizing abrasion and tears that potentially can damage the person wearing the APG garment. Such fibers may be used in a helmet to enhance head protection. The fibers may be permanently affixed to the helmet or hat or they may be selectively retractable or extendable based on determination of a dangerous condition by a logic controller. Materials suitable for such fibers include, but are not limited to, steel, polyester, polytetrafluoroethylene, polyolefin, Kevlar, and the like. The fibers are a suitable enhancement for the protection afforded by the APG collar 70, the APG pants 90, or the APG coat 80. The fiber length ranges from 0.1 inches to 3.0 inches and preferably from 0.25 inches to 1.0 inches. The fiber density is preferably sufficient to visually obscure more than 50% of the surface of the APG garment.

The APG garment may be washable and specifically machine washable. The logic controller and power supply are unplugged from the electrical bus prior to cleaning. The pressurized gas sources and valves, as well as the accelerometers and gyroscopes are sealed to allow for cleaning without loss of function.

Figure 10:
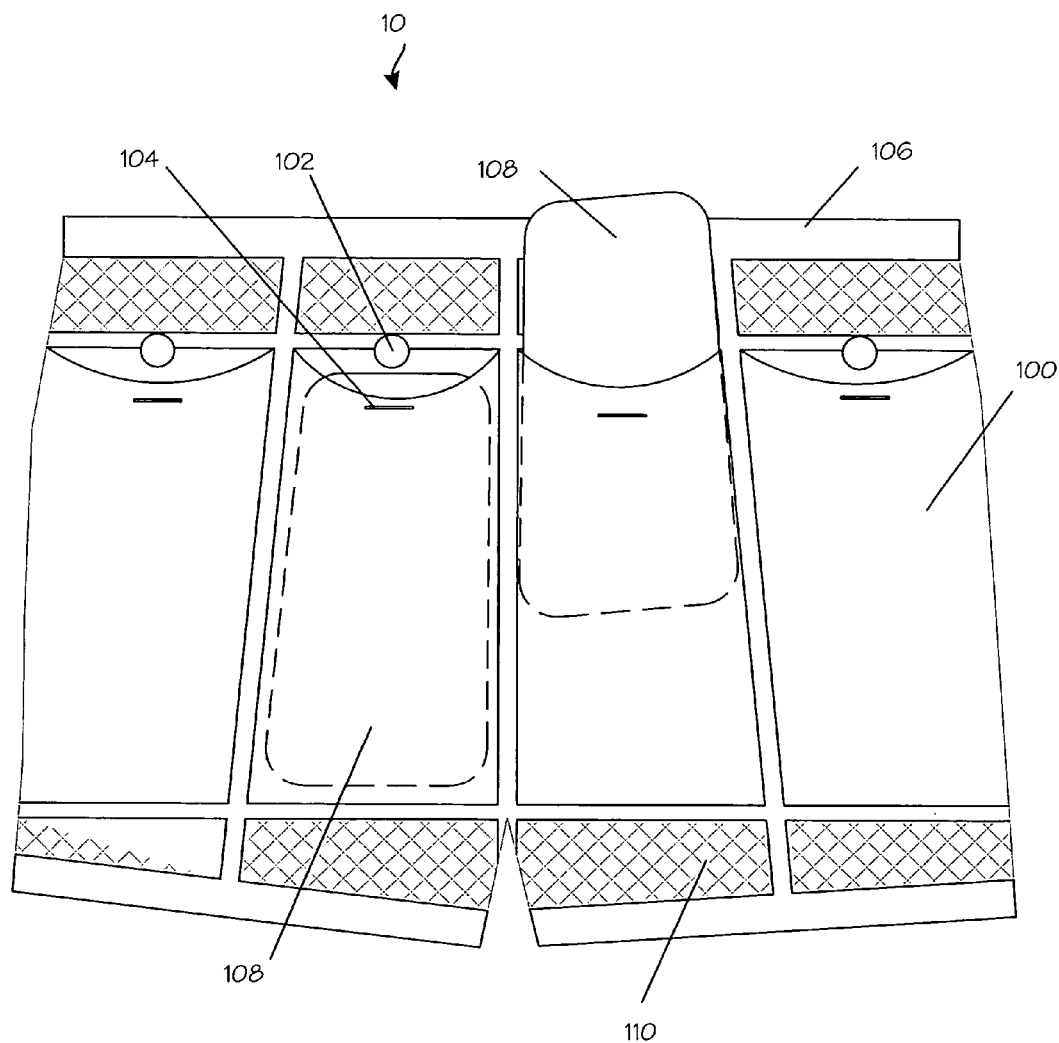
FIG. 10 illustrates a rear view of a pair of APG shorts with pockets into which APG components are inserted.

In FIG. 10, a pair of APG shorts 10 are shown in rear view. The APG shorts 10 further comprise a plurality of pockets 100, a plurality of fasteners 102, a plurality of fastener holes 104, a base garment 106, a plurality of removable isolated APG chambers 108, and a plurality of breathable regions 110.

Referring to FIGS. 3 and 10, the removable isolated APG chambers 108 further comprise one or more accelerometers 14, and/or one or more gyroscopes 16 or rotational accelerometers. The removable isolated APG chambers 108 further comprise a power supply 24, a logic controller 22, a high pressure or compressed gas source 18 and an actuable valve 20 or airbag inflator. The actuable valve 20 or airbag inflator and the accelerometers 14 or gyroscopes 16 are preferably hard wired electrically to the logic controller 22. All components are preferably affixed to the interior surface of the removable isolated APG chambers 108. The logic controller 22 further comprises wireless communication subsystems for short-range communication with other removable isolated APG chambers 108 removably affixed to the base garment 106 by being inserted into the pockets 100, which are integral to the base garment, and secured in place by fasteners 102 and fastener holes 104.

Referring to FIGS. 3 and 10, the wireless communication between the logic controllers 22 on each of the APG chambers 108 is made by methods including, but not limited to, microwave, infrared, ultrasonic, radio waves or similar. The transmissions are preferably digitally encoded to minimize the risk of interference from outside sources. The logic controllers 22 preferably comprise fail-safe mechanisms to activate upon impact but primarily activate upon determination of a fall in progress as evidenced by accelerometer or gyroscope data.

The APG shorts 10 illustrated in FIG. 10 are beneficial because the isolated APG chambers 108 are removable and the base garment 106 is washable. The number of breathable regions 110 is maximized in this configuration to enhance comfort and wearability of the APG shorts 10.

The fasteners 102 and fastener holes 104 comprised in the base garment 106 are illustrative of typical fasteners. Other fasteners suitable for this application include but are not limited to, Velcro, snaps, zippers, and the like.

The APG may comprise three each three-dimensional accelerometers. These accelerometers each read in the X, Y, and Z axis. The three-dimensional accelerometers are located one at the base of the neck, one at the right hip and one at the left hip. The three accelerometers feed nine channels of acceleration data into the onboard logic controller or computer through digital input or analog to digital converters. The logic controller or computer takes the derivative of the signals over time to provide velocity, and takes the derivative of the velocity data over time to provide distance. The acceleration, velocity, and distance data are constantly evaluated by a rule-based system that determines whether the measured parameters are within the range of normal safe human motion or whether a fall in progress is occurring and thus triggering activation of a protective device.

This further comprises an optional sonar, proximity, or position sensor to detect proximity to objects and for calibration of the accelerometers. This type of sensor is capable of detection of injurious falls by combining proximity detection (the distance from an object) and closing velocity detection (speed at which an object is being approached). Such a sensor utilizes basic sonar techniques by emitting a set of ultrasonic pulses whose echo is used to perform both measurements. The basic device consists of an ultrasonic transmitter (or transmitters) and a corresponding ultrasonic receiver (or receivers). The basic principle of operation is for the transmitter to periodically emit a set of ultrasonic pulses, which will bounce off of any nearby solid object. These pulses bounce off of nearby solid objects and return to be detected by the receiver. Distance is determined by the time taken for the audio return signal. Velocity is determined by the change in return time (corresponding to a change in distance) between different pulse groups (corresponding to a change in time).

The ultrasonic transmitter should operate in the range between 40 KHz and 70 KHz. This frequency range is roughly the middle of the range used by Bats and is sufficiently above the human hearing range to avoid any negative sensations. High frequency is also more effective at close range measurements and does not propagate as effectively through barriers such as doors and walls (a desirable characteristic).

Simple distance measurement is possible. The velocity of sound is roughly 700 miles per hour or 1027 feet per second. This results in sound traveling 1 foot in approximately 0.97 milliseconds. For a round trip reflection off of a hard surface from a 2-foot distance would be 3.9 milliseconds while from 1 foot would be 1.95 milliseconds. This is well within the range of almost any microprocessor or digital signal processor on the market today.

The approach velocity of concern for falls is in the range of 4 miles per hour or 5.9 feet per second. The final foot of an injurious fall would take approximately 0.17 seconds. There is sufficient time for more than 40 complete echo pulses to be transmitted and received during this period of time. Velocity is calculated by determining the difference between the echo time (distance measurement) of one echo group and the next. For example if echo pulses are emitted at 0.1 seconds apart and the closing distance to an object is 4 miles per hour, the change in the echo time is more than 1 millisecond for each pulse (See Table 1 for the complete closing sequence). Again this is very practical set of times and calculations to perform for any microprocessor or digital signal processor.

TABLE 1

Echo Times for the last second of a 4.0 MPH approach velocity

| Time (sec) | Distance (feet) | Echo (ms) |
|---|---|---|
| 1 | 5.87 | 11.43 |
| 0.9 | 5.28 | 10.29 |
| 0.8 | 4.69 | 9.14 |
| 0.7 | 4.11 | 8.00 |
| 0.6 | 3.52 | 6.86 |
| 0.5 | 2.93 | 5.71 |
| 0.4 | 2.35 | 4.57 |
| 0.3 | 1.76 | 3.43 |
| 0.2 | 1.17 | 2.29 |
| 0.1 | 0.59 | 1.14 |

The time between echo pulse groups can be varied based on distance. When the distance is great, the pulses can be far apart to conserve energy. As the distance gets closer, the echo pulse group rate can be increased to provide increased accuracy for both distance and velocity. This approach is useful in conserving battery power or system energy.

A single frequency/single pulse technique would be very simple but is highly subject to interference. The transmitted ultrasonic signal should be a combination of several short pulses at detectably different frequencies. This technique will prevent any single interference source from disabling the detector. A second significant type of potential interference is objects directly adjacent (such as sitting in a chair, leaning against a wall, etc.). Sonar techniques have a characteristic blind spot preventing the detection of objects very close to the transmitter/receiver. The existence of this characteristic blind spot prevents directly adjacent objects from creating any interference.

The potential for false positives (trigging a pending impact condition at excessive velocity) must be carefully evaluated. Concern has been expressed about the potential of a false trigger when a person walks past a solid object (but does not impact the object). In general if the approach velocity is below the identified injurious velocity, then no potential for a false trigger exists. Efficiency of the sensor is increased when it is determined if normal daily activity creates velocities, which exceed the critical injurious velocity. Initial review of material indicates that there is indeed a gap between normal daily activity velocities and an injurious velocity especially for people in the age and activity group to which these detection devices would apply. Nevertheless, the concept of utilizing multiple dissimilar sensors of which the proximity/velocity sensor is part of a system, which will provide a high degree of reliability while minimizing the potential for being a nuisance to the user.

The digital signal processor, logic controller or computer may comprise software and hardware that allows for a training mode. In this mode, the APG is worn by the patient and the patient goes through a series of defined or undefined movements representing normal daily movement for that individual. This information is used to define parameters of the rule-based system or neural net software that monitors the APG sensors and determines whether or not to activate protective mechanisms. The training mode is generally enabled by a caregiver by generating input code to the computer or by activating a switch which starts training mode. Training mode is activated and deactivated by a manual switch but such switching can be either automatic, timed, or software-driven.

The training mode comprises three basic requirements. First, the manufacturer of the APG predetermines a set of acceleration profiles and programs those into the APG. These acceleration profiles represent several common activities that can be classified as a falling condition for a majority of people. By way of example, the manufacturer may preset a set of acceleration profiles defining a) slipping on ice; b) tripping forward; and c) jumping off a diving board. The APG is then sold to a user, containing the preset profiles. The user can then elect to input his own particular or individual set of acceleration profiles. The user identifies to the APG that the input activities define "normal" or "routine" activities for the particular user. They are "normal" or "routine" for the user in that they do not represent activities where the user is actually falling. If any of these user set profiles coincide with any of the manufacturers preset profiles, the user removes the preset activity as a condition for deployment of the gas source. As a result, the user can engage in any routine activity without fear of deployment of the APG.

The sensors can be calibrated with respect to a preassigned baseline. This calibration is either done with the aforementioned training mode, or by use of other transducers or external reference points. A patient may be fitted with the APG and a caregiver uses external instrumentation to measure the exact locations of the sensors or implants that guide location of the sensors. A sonar or position device may be used to determine the position of each transducer (accelerometer, other position sensor, rotational sensors, etc.) or certain reference points on the patient.

The APG system may provide a self-test function to ensure that all systems are within normal operating parameters. This self-test can be manually activated, automatically activated, or activated on a timed basis, once a day, for example. The APG system, further comprises on-off switching to disable the system as desired. This on-off function can be set so that only a caregiver can operate it or it can be set that the patient can also operate the on-off function.

The accelerometers or sensors may be taped to the body, implanted subcutaneously or intramuscularly. Power is transmitted to the sensors transcutaneously through coils or through RF ID type systems with antennas distributed within at least a portion of the active protective garment. The computer and power supply are external and part of the garment. Implanted devices may serve as positioning clips or locating devices to ensure placement of the sensors at the correct location on the body. Such implanted devices may comprise magnets, partially protruding attachment knobs or points, or electronically communicating RF ID device.

The accelerometers, linear or rotational, but especially linear, are separated by distance sufficient to generate relative motions. The accelerometer should be spaced to generate data from different parts of the body, particularly the torso. The spacing of the accelerometers may be one on the left hip, one on the right hip, and one at or near the neck. Other configurations are also appropriate, so long as the accelerometers are placed at some distance apart from each other so that they are able to discriminate the rotational data readings from each accelerometer. Three each three-dimensional accelerometers spaced in this configuration can translate in three axes at their locations as well as rotations about all three major axes. The accelerometers can be placed on a part of the body where the relative positions remain relatively constant so that rotational accelerations, rotational velocities and distances can be calculated with minimal errors caused by changes in spacing.

The system may comprise one or more algorithms, which is a software, firmware, or hardware. An exemplary algorithm for a typical slipping fall backward will trigger activation of the device if the following conditions are met:
1) Both hip accelerometers receive initially little downward acceleration (normal status);
2) the neck accelerometer accelerates posteriorly in the anterior-posterior plane of the patient while the hip accelerometers accelerate, simultaneously with the neck accelerometer, anteriorly or not at all;
3) the hip accelerometers begin accelerating toward the ground or in a direction towards the feet with some posterior component with composite vertical velocities (calculated by taking the derivative of acceleration over time) reaching greater than 1 meter per second;
4) the neck accelerometer continues to measure accelerations in the posterior direction with the derivative overall velocities exceeding 1 meter per second;
5) the activation of the triggering mechanism for the airbag will occur once velocities exceed 1 meter per second in order to allow time for the protection device (airbag) to inflate and protect the wearer.
6) As aggregate or composite velocities approach 2 meters per second, an impact is imminent.

Another exemplary algorithm for a typical tripping fall forward if the following conditions are met is:
1) both hip accelerometers receive initially little downward acceleration (normal status);
2) the neck accelerometer suddenly accelerates anteriorly in the anterior-posterior plane of the wearer while the hip accelerometers accelerate, simultaneously with the neck accelerometer, only slightly anteriorly or not at all;

3) the neck accelerometer continues to accelerate and reaches the derivative velocities in excess of 1 meter per second at which point triggering of the protection device is activated;

4) the hip accelerometers provide similar anterior acceleration measurements relative to each other but measure far less acceleration than the neck accelerometer indicative of high velocity rotation and imminent fall.

As another example, should composite velocities exceeding negative 1 meter per second occur without the relative rotation of the neck relative to the hips, activation of the protection mechanism would not be warranted. Such a condition could occur only in a car or other moving vehicle, jumping off a substantial height, etc.

The APG shorts 10 may include a GPS system and a transmitter suitable for communications with cell phone systems to notify other people or emergency people that a fall has occurred and the APG shorts were activated. Inter-APG signals may be transmitted via wires or by wireless methods. The Active Protective Garment may be a coat, pants, shirt, vest, helmet, or other type of clothing. The system may be designed to protect the wearer from a fall from standing, from bed, from being thrown off a motorcycle or bicycle, or it may protect the wearer from falling a substantial distance such as 10 to 30 feet.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. An air bag inflation device adapted for preventing injury to a wearer, said device comprising:
    a garment worn by the wearer;
    a bladder coupled to the garment;
    at least one releasable source of gas coupled to the bladder;
    a plurality of sensors positioned on the wearer for measuring acceleration of the device wherein the acceleration is measured at predetermined intervals;
    a data storage media for recording the acceleration measurement readings;
    a logic controller that is adapted to receive the acceleration readings from the data storage media and perform a calculation to determine when the wearer is falling;
    a means for discharging the source of gas from the source into the bladder upon the determination of the logic controller that the wearer is falling; and
    a means for measuring rotation of the device wherein the rotation is measured at predetermined intervals and recorded in the data storage media.

2. The device of claim 1 further comprising a communication device coupled to the logic controller that notifies emergency personnel when a wearer falls.

3. The device of claim 1 wherein the logic controller is adapted to receive the rotation measurement readings from the data storage media and perform a calculation to determine when the wearer is falling.

4. The device of claim 3 wherein the plurality of sensors configure one on the wearer's neck, one on the left hip, and one on the right hip.

5. The device of claim 4 wherein the logic controller performs a calculation to determine when a wearer is falling according to the following:
    a) the neck sensor accelerates in a direction and at least one of the hip sensors accelerate in an opposite direction to that of the neck sensor;
    b) the hip sensor accelerates in a direction toward the user's feet, the first integral of the acceleration over time defines a vertical velocity, and the vertical velocity is greater than 1 meter per second; and
    c) the neck sensor accelerates, the first integral of acceleration over time defines a vertical velocity, and the vertical velocity is greater than 1 meter per second.

6. The device of claim 4 wherein the logic controller performs a calculation to determine when a wearer is falling according to the following:
    a) the neck sensor accelerates in a direction and at least one of the hip sensors accelerate in the same direction;
    b) the neck sensor continues to accelerate, the first integral of the acceleration over time defines a vertical velocity, and the vertical velocity is greater than 1 meter per second; and
    c) one or both of the hip sensors continue to accelerate relative to each other but accelerate less than the neck sensor.

7. The device of claim 4 wherein the logic controller performs a calculation to determine when a wearer is falling according to the following:
    a) the neck sensor accelerates in a direction and at least one of the hip sensors do not accelerate;
    b) the neck sensor continues to accelerate, the first integral of the acceleration over time defines a vertical velocity, and the vertical velocity is greater than 1 meter per second; and
    c) at least one of the hip sensors continue to accelerate relative to the other hip sensor but accelerate less than the neck sensor.

8. The device of claim 4 wherein the logic controller performs a calculation to determine when a wearer is falling according to the condition that the rotation rate between the hip and neck sensors exceeds 45 degrees in 0.1 seconds.

9. The device of claim 4 wherein the logic controller performs a calculation to determine when a wearer is falling according to the parameter that the acceleration readings integrated over time are the vertical velocity and the vertical velocity of each sensor is of a magnitude greater than negative one meter per second.

10. The device of claim 4 wherein the logic controller performs a calculation to determine when a wearer is falling according to the parameter that acceleration readings derived over time are vertical velocity and the vertical velocity of each sensor is greater than one meter per second and moves from positive vertical velocity to negative vertical velocity in less than 0.25 seconds.

11. The device of claim 1 wherein the logic controller is adapted to be programmed by an individual wearer to store the individual's own acceleration and rotation settings in routine movements within the logic controller so that the individual settings do not trigger deployment of the device.

12. The device of claim 1 wherein the means for discharging the source of gas from the source into the bladder is an igniter.

13. The device of claim 12 further comprising a valve coupled to the gas source and the igniter wherein the valve releases the flow of gas into a cavity upon the determination of the logic controller that the wearer is falling.

* * * * *

UNITED STATES PATENT AND TRADEMARK OFFICE
CERTIFICATE OF CORRECTION

PATENT NO. : 7,017,195 B2
APPLICATION NO. : 10/741639
DATED : March 28, 2006
INVENTOR(S) : Robert F. Buckman, Jay A. Lenker and Richard E. Reedy Page 1 of 1

It is certified that error appears in the above-identified patent and that said Letters Patent is hereby corrected as shown below:

On the Title Page

Item (76) (Inventors), please correct:
"Inventors: Robert F. Buckman, 125 Chew La., Radnor, PA (US) 19087-5207; Jay A. Lenker, 408 Panorama Dr., Laguna Beach, CA (US) 92651; Donald J. Kolehmainen, 6 Crested Butte Cir., Laguna Niguel, CA (US) 92677"
To read as follows:
--Robert F. Buckman, 125 Chew La., Radnor, PA (US) 19087-5207; Jay A. Lenker, 408 Panorama Dr., Laguna Beach, CA (US) 92651; Richard E. Reedy, 2275 Hillview Drive, Laguna Beach, CA (US) 92651--

Signed and Sealed this
Eighteenth Day of August, 2020

Andrei Iancu
*Director of the United States Patent and Trademark Office*